(12) United States Patent
Yoo et al.

(10) Patent No.: US 8,404,869 B2
(45) Date of Patent: *Mar. 26, 2013

(54) PHENANTHRENEQUINONE-BASED COMPOUND AND PHARMACEUTICAL COMPOSITION CONTAINING THE SAME FOR THE TREATMENT OR PREVENTION OF DISEASE INVOLVING METABOLIC SYNDROME

(75) Inventors: Sang-Ku Yoo, Gwacheon-shi (KR); Ku Suk Kang, Siheung-shi (KR); Sang Woo Yoo, Seoul (KR); Taehwan Kwak, Yongin-shi (KR)

(73) Assignees: Mazence Inc., Daejeon (KR); KT & G Co., Ltd., Daejeon (KR)

( * ) Notice: Subject to any disclaimer, the term of this patent is extended or adjusted under 35 U.S.C. 154(b) by 546 days.

This patent is subject to a terminal disclaimer.

(21) Appl. No.: 12/597,414

(22) PCT Filed: Apr. 25, 2008

(86) PCT No.: PCT/KR2008/002348
§ 371 (c)(1),
(2), (4) Date: Oct. 23, 2009

(87) PCT Pub. No.: WO2008/133441
PCT Pub. Date: Nov. 6, 2008

(65) Prior Publication Data
US 2010/0137422 A1 Jun. 3, 2010

(30) Foreign Application Priority Data
Apr. 26, 2007 (KR) .................. 10-2007-0040673

(51) Int. Cl.
C07D 311/78 (2006.01)
A61K 31/35 (2006.01)
(52) U.S. Cl. ......... 549/384; 549/457; 514/453; 514/463
(58) Field of Classification Search .................. 549/384, 549/457; 514/453, 463
See application file for complete search history.

(56) References Cited

U.S. PATENT DOCUMENTS
2007/0248698 A1 10/2007 Kwak et al.

FOREIGN PATENT DOCUMENTS

| KR | 10-2003-0099556 | 12/2003 |
|---|---|---|
| KR | 10-2003-0099557 | 12/2003 |
| KR | 10-2003-0099657 | 12/2003 |
| KR | 10-2003-0099658 | 12/2003 |
| KR | 10-2004-0036195 | 5/2004 |
| KR | 10-2004-0036197 | 5/2004 |
| KR | 10-2004-0050200 | 6/2004 |
| KR | 10-2004-0116339 | 7/2005 |
| KR | 10-2006-0014541 | 8/2006 |
| WO | WO 2005/063232 * | 7/2005 ............ 549/384 |
| WO | WO-2005/063232 A1 | 7/2005 |
| WO | WO-2008/066294 A1 | 6/2008 |

OTHER PUBLICATIONS

Lee et al, Tetra. Let. vol. 28 No. 30, pp. 3427-3430 (1987).*
Han, AAPS Pharnsci (2000), vol. 2 No. 1 article 6.*
Ettmayer et al, Jor. Med. Chem. vol. 47, No. 10 pp. 2393-2404 (2004).*
Kim et al., "Antidiabetes and Antiobesity Effect of Cryptotanshinone via Activation of AMP—Activated Protein Kinase," Molecular Pharmacology, The American Society for Pharmacology and Experimental Therapeutics, vol. 72, No. 1, pp. 62-72, 2007.
Fieser, "Some Derivatives of 3,4-Phenanthrenequinone", Journal of the American Chemical Society, 1929, vol. 51, pp. 940-952.
Sairafianpour et al., "Leishmanicidal, Antiplasmodial, and Cytotoxic Activity of Novel Diterpenoid 1,2-Quinones from *Perovskia abrotanoides*: New Source of Tanshinones", Journal of Natural Products, 2001, vol. 64, No. 11, pp. 1398-1403.
Ruderman et al., "AMP Kinase and Malonyl-COA: Targets for Therapy of the Metabolic Syndrome," Nature Reviews, vol. 3, Apr. 2004, pp. 340-351.
Unger, "The Hyperieptinemia of Obesity-Regulator fo Caloric Surpluses," Cell, vol. 117, Apr. 16, 2004, pp. 145-151.
Lee et al., "Vascular endothelial growth factor (VEGF) induces remodeling and enhances $T_H2$-medicated sensitization and inflammation in the lung," Nature Medicine, vol. 10, No. 10, Oct. 2004, pp. 1095-1103.
Diraison et al., "Impact of Adenovirai Transduction With SREBP1c or AMPK on Pancreatic Islet Gene Expression Profile: Analysis With Oligonucleotide Microarrays," Diabetes, vol. 53, Supplement 3, Dec. 2004; pp. S84-S91.
Sambandam et al., "AMP—activated protein kinase (AMPK) control of fatty acid and glucose metabolism in the ischemic heart," Progress in Lipid Research, vol. 42, 2003, pp. 238-256.
You et al., "Recent Advances in Alcoholic Liver Disease, II. Minireview: molecular mechanisms of alcoholic fatty liver," Am. J. Physiol, Gastrointest Liver Physiol, vol. 287, 2004, pp. G1-G6.
Pilon et al.. "Inhibition of Inducible Nitric-oxide Synthase by Activators of AMP-activated Protein Kinase," The Journal of Biological Chemistry, vol. 279, No. 20, Issue of May 14, 2004, pp. 20767-20774.
Chen et al., "AMP—activated protein kinase phosphorylation of endothelial NO synthase." FEBS Letters, vol. 443, 1999, pp. 285-289.
Apfeld et al., "The AMP—activated protein kinase AAK-2 links energy levels and insulin-like signals to lifespan in *C. elegans*," Genes & Development, vol. 18, pp. 3004-3009, 2004.

* cited by examiner

*Primary Examiner* — Andrew D Kosar
*Assistant Examiner* — Raymond Covington
(74) *Attorney, Agent, or Firm* — Birch, Stewart, Kolasch & Birch, LLP

(57) ABSTRACT

Provided is a pharmaceutical composition for the treatment and/or prevention of disease involving metabolic syndromes, comprising (a) a therapeutically effective amount of a particular compound represented by Formula 1 as defined in the specification, or isomer, prodrug, or solvate or thereof, and (b) a pharmaceutically acceptable carrier, a diluent or an excipient, or any combination thereof.

15 Claims, 3 Drawing Sheets

PHENANTHRENEQUINONE-BASED COMPOUND AND PHARMACEUTICAL COMPOSITION CONTAINING THE SAME FOR THE TREATMENT OR PREVENTION OF DISEASE INVOLVING METABOLIC SYNDROME

FIELD OF THE INVENTION

The present invention relates to novel phenanthrenequinone-based compounds which may be used as the treatment or prevention of diseases involving metabolic syndrome and pharmaceutical composition containing the Same.

BACKGROUND OF THE INVENTION

Metabolic syndrome is a comprehensive manifestation that refers to syndrome involving health risk factors such as hypertriglyceridemia, hypertension, glycometabolism disorder, blood coagulation disorder and obesity. Metabolic syndrome itself is not fatal, but indicates a predisposition to severe diseases such as diabetes and ischemic cardiovascular diseases, and is understood as the most threatening diseases among modern people. Not long ago, Metabolic syndrome was known by various other names including Syndrome X, due to lack of knowledge about causes of such syndrome, but was officially designated as Metabolic Syndrome or Insulin Resistance Syndrome through Adult Treatment Program III (ATP III) enacted by the WHO and the National Heart, Lung, and Blood Institute of the NIH.

Insulin resistance refers to a phenomenon wherein, even though insulin is normally secreted in vivo, insulin does not induce sufficient supply of glucose to cells. Therefore, in case of person having insulin resistance, glucose in the blood is not absorbed into cells, thus causing hyperglycemia, thereby cells leading to the manifestation of metabolic syndrome which cannot perform normal functions due to a shortage of glucose.

At present, there are no drugs available for the treatment of metabolic syndrome. Attempts have been made to treat metabolic syndrome using therapeutic agents for diabetes, hyperlipidemia and hypertension, but these drugs have limited effectiveness in treating metabolic syndrome as the drug. As currently available drugs, metformin, drugs belonging to the TZD (thiazolidinediones) family, glucosidase inhibitors, dual PPARγ/α agonists and DDP (Dipeptidyl peptidase) IV inhibitors, which are used for the treatment of diabetes, have received a great deal of attention as promising drugs for treating metabolic syndrome. In addition, a great deal of interest has been directed to isoforms of apoA-I and related peptides thereof, which are targets of anti-blood pressure drugs and anti-hyperlipidemic drugs, and CETP (Cholesterol ester transport protein) inhibitors. These drugs which can treat with metabolic syndrome are known to show common effect that AMPK is activated. Among the drugs as referred above, metformin and TZD drugs are also belong to this class. For this reason, the present inventors have also employed a method of confirming the presence/absence of activation effects on AMP-activated protein kinase (AMPK), as the most fundamental primary test to confirm biological efficacy of compounds of interest on disease syndromes.

In this way, AMPK is known to play a central role in energy metabolism of glucose, protein and fat in vitro and in vivo. Neil, et al (Nature drug discovery, 3(Apr.), 340, 2004) has asserted that AMPK and Malonyl-CoA are possible targets for the treatment of metabolic syndromes, and they have also stated that patients suffering from metabolic syndromes can be characterized by insulin resistance, obesity, hypertension, dyslipidemia, and dysfunction of pancreatic beta cells, type II diabetes and manifestation of arteriosclerosis. It was hypothesized that a common feature linking these multiple abnormalities is dysregulation of AMPK/Malonyl-CoA energy level-sensing and signaling network. It was proposed that such dysregulation leads to alterations in cellular fatty-acid metabolism that in turn cause abnormal fat accumulation, cellular dysfunction and ultimately disease. Evidence is also presented that factors activating AMPK and/or reducing malonyl-CoA levels might reverse these abnormalities and syndromes or prevent incidence of these diseases.

Roger, et al (Cell, 117, 145-151, 2004) have suggested that AMPK may be a possible target to control obesity by lowering activity of hypothalamic AMPK, thereby increasing a content of malonyl-CoA and then regulating appetite for food intake.

Lee, et al (Nature medicine, 13(Jun.), 2004) have suggested that alpha-lipoic acid can exert anti-obesity effects by suppressing hypothalamic AMPK activity, thus controlling appetite. They have also reported that alpha-lipoic acid promotes fat metabolism via activation of AMPK in muscle tissues, not hypothalamus, and alpha-lipoic acid is therapeutically effective for the treatment of obesity because it facilitates energy expenditure by activating UCP-1, particularly in adipocytes.

Diraison, et al (Diabetes 53, S84-91, 2004) have reported that activation of AMPK in pancreatic cells leads to four-fold increases in expression of the gut hormone peptide YY responsible for appetite control and thus appetite can be regulated by the action of AMPK in other tissues other than hypothalamus.

Nandakumar, et al (Progress in lipid research 42, 238-256, 2003) have proposed that, in ischemic heart diseases, AMPK would be a target to treat ischemia reperfusion injuries via regulation of fat and glucose metabolism.

Min, et al (Am. J. Physiol. Gastrointest Liver Physiol 287, G1-6, 2004) have reported that AMPK is effective for regulation of alcoholic fatty liver.

Genevieve, et al (J. Biol. Chem. 279, 20767-74, 2004) have reported that activation of AMPK inhibits activity of an iNOS enzyme that is an inflammation mediator in chronic inflammatory conditions or endotoxin shock, including obesity-related diabetes and thus AMPK will be effective for developing new medicines having a mechanism capable of enhancing insulin sensitivity. In addition, they have reported that inhibition of iNOS activity is effected by activation of AMPK, and thus this finding is clinically applicable to diseases such as septicemia, multiple sclerosis, myocardial infarction, inflammatory bowel diseases and pancreatic beta-cell dysfunction.

Zing-ping et al (FEBS Letters 443, 285-289, 1999) have reported that AMPK activates endothelial NO synthase through phosphorylation, in the presence of Ca-calmodulin in murine muscle cells and myocardial cells. This represents that AMPK is implicated in heart diseases including angina pectoris.

Javier, et al (Genes & Develop. 2004) have reported that a lifespan can be extended by limiting utilization of energy and such a prolonged lifespan is achieved in a manner that an in vivo AMP/ATP ratio is increased and therefore the α2 subunit of AMPK is activated by AMP. Therefore, they have suggested that AMPK may function as a sensor to detect the relationship between lifespan extension and energy level and insulin-like signal information.

Meanwhile, Danshen (*Salvia miltiorrhiza*) has been widely used as an important herbal medicine in Northeast Asia regions since ancient times, and is well-known to have excellent effects on the prevention and treatment of various cardiovascular diseases. Upon focusing our attention to such therapeutic efficacy of Danshen, the inventors of the present invention have suggested that main ingredients of Danshen are superb medicinal substances capable of treating various diseases such as obesity, diabetes and metabolic syndromes. For example, see Korean Patent Nos. 2003-0099556, 2003-0099557, 2003-0099657, 2003-0099658, 2004-0036195, 2004-0036197 and 2004-0050200, assigned to the present applicant. In particular, the present inventors have revealed that main principles of Danshen including Cryptotanshinone, 15,16-Dihydrotanshinone can treat metabolic syndrome diseases.

B, lantalucratin A, lantalucratin B and lantalucratin C not only have chemical functional group which is the same as or similar to Cryptotanshinone and Dihydrotanshinon and the like, but also have pharmacological actions as therapeutic and prophylactic agents for disease involving metabolic syndrome.

That is, the present inventor has attempted to examine whether naphthoquinone-based compounds as disclosed in the present invention activate AMPK in cells and tissues. Then, in order to examine profoundly therapeutic effects of the compounds for disease syndromes diseases based on results thus obtained, the present inventor have examined therapeutic effects for the treatment and/or prevention of disease involving metabolic syndromes including obesity and diabetes through various experiments using OB mice, a animal model of obesity caused by decreased secretion of leptin.

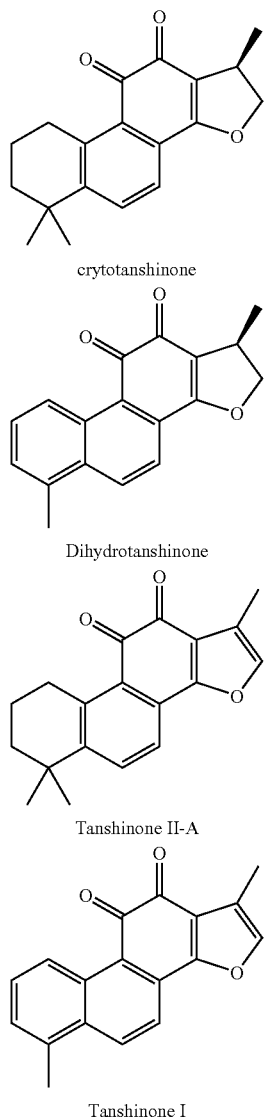

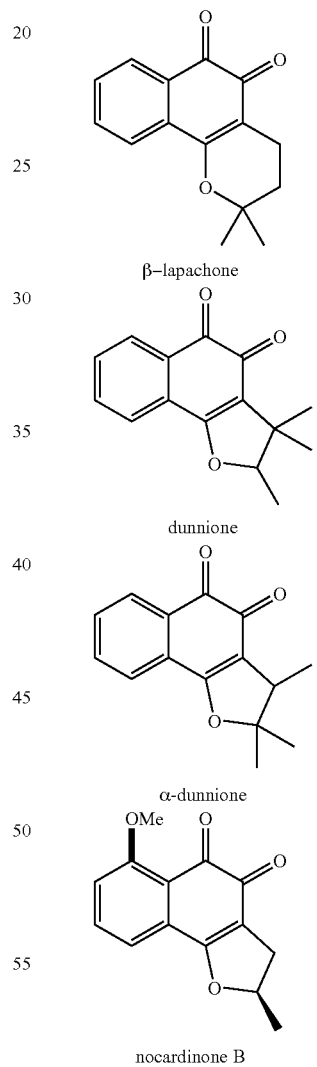

The inventors of the present invention have newly confirmed that novel naphthoquinone-based compounds such as β-lapachone {7,8-dihydro-2,2-dimethyl-2H-naphtho(2,3-b)dihydropyran-7,8-dione}, dunnione {2,3,3-tirmethyl-2,3,4,5-tetrahydro-naphtho(2,3-b)dihydrofuran-6,7-dione}, α-dunnione {2,3,3-tirmethyl-2,3,4,5-tetrahydro-naphtho(2,3-b)dihydrofuran-6,7-dione}, nocardinone A, nocardinone

SUMMARY OF THE INVENTION

Thus, the inventors of the present invention have investigated various derivatives of Cryptotanshinone and Dihydrotanshinon, their pharmacological actions as therapeutic and prophylactic agents for disease involving metabolic syndromes which can also be used in the prevention or treatment of disease involving metabolic syndromes, and have attempted to examine whether phenanthrenequinone-based compounds of novel structure activate AMPK in cells and tissues. Then, in order to examine profoundly therapeutic effects of the compounds for disease involving metabolic syndromes diseases based on results thus obtained, the present inventors have examined therapeutic effects for the treatment and/or prevention of disease involving metabolic syndromes including obesity and diabetes, through various experiments using OB mice, a animal model of obesity caused by decreased secretion of leptin. Consequently, the present inventors have confirmed that the novel phenanthrenequinone-based compounds in accordance with the present invention have excellent effects on the treatment and/or prevention of disease involving metabolic syndromes. The present invention has been completed based on these findings.

Therefore, an object of the present invention is to provide a pharmaceutical composition comprising, as an active ingredient, phenanthrenequinone-based compound which is therapeutically effective for the treatment and prevention of disease involving metabolic syndromes.

In accordance with an aspect of the present invention, the above and other objects can be accomplished by the provision of a pharmaceutical composition for the treatment and/or prevention of disease involving metabolic syndromes, providing: (a) a therapeutically effective amount of a compound represented by Formula I below:

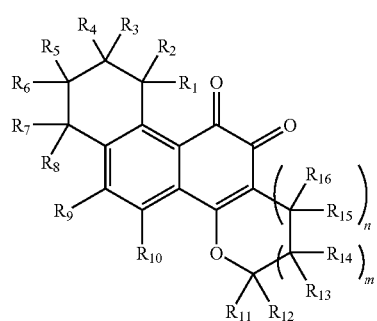

(1)

wherein $R_1$, $R_2$, $R_3$, $R_4$, $R_5$, $R_6$, $R_7$ and $R_8$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl, or heterocycloalkyl, $C_4$-$C_{10}$ aryl or heteroaryl, or two substituents thereof may be taken together to form a cyclic structure or form a double bond;

$R_9$ and $R_{10}$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl, or heterocycloalkyl, $C_4$-$C_{10}$ aryl or heteroaryl;

$R_{11}$, $R_{12}$, $R_{13}$, $R_{14}$, $R_{15}$ and $R_{16}$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl, or heterocycloalkyl, $C_4$-$C_{10}$ aryl or heteroaryl, or two substituents thereof may be taken together to form a cyclic structure or form a double bond;

m and n are each independently 0 or 1, when m or n is 0, carbon atoms adjacent to m or n may form a cyclic structure via a direct bond;

in the condition that m is 1, n is 0, carbon atoms adjacent to m or n form a cyclic structure via a direct bond, $R_9$, $R_{10}$ and $R_{11}$ are hydrogen, and $R_{12}$ and $R_{13}$ are hydrogen or are taken together to form a double bond, (i) when $R_1$ to $R_6$ are hydrogen and $R_7$ and $R_8$ are methyl, $R_{14}$ is not methyl, and (ii) when $R_1$, $R_3$ and $R_5$ are hydrogen and $R_2$, $R_4$, $R_6$ and $R_8$ are taken together to form a double bond and $R_7$ is methyl, $R_{14}$ is not methyl; and (b) a pharmaceutically acceptable carrier, a diluent, an excipient, or any combination thereof.

The present inventors have confirmed therapeutic effects of the compound of Formula I on metabolic syndrome, as will be illustrated in Experimental Examples hereinafter, have measured activity of the compound of Formula I on AMPK activity in myoblast cells (C2C12) and suppression of cellular differentiation in preadipocytes (3T3-L1 and F442A cells) and as a result, have confirmed that such a compound exhibits superior AMPK activation effects and inhibitory effects of adipocyte differentiation.

In addition, the present inventors have further confirmed that therapeutic and prophylactic effects of metabolic syndromes by the compound of Formula I were examined through in vivo experiments which relate to the treatment and prevention of metabolic syndromes, using OB mice as a model of obesity, db/db mice as a model of obesity/diabetes, DIO (diet-induced obesity) mice, caused by high fat dietary conditions, and Zucker fa/fa rats as a model of obesity/diabetes, and as a result, the compound of Formula I was highly therapeutically effective.

Further, the compound of Formula I was confirmed to exert significant synergistic effect, compared with tanshinone derivatives extracted from Danshen in light of weight loss against an animal model of obesity.

Therefore, it is expected that the composition for treating and preventing metabolic syndrome, comprising the compound of Formula I as an active ingredient, can treat and prevent a metabolic syndrome, via activation of AMPK.

As used herein, the term "isomer" means a compound of the present invention or a salt thereof, that has the same chemical formula or molecular formula but is optically or sterically different therefrom. D type optical isomer and L type optical isomer can be present in the Formula 1, depending on the types of $R_1$~$R_{16}$ substituents selected.

As used herein, the term "prodrug" means an agent that is converted into the parent drug in vivo. Prodrugs are often useful because, in some situations, they may be easier to administer than the parent drug. They may, for instance, be bioavailable by oral administration, whereas the parent may be not. The prodrugs may also have improved solubility in pharmaceutical compositions over the parent drug. An example of a prodrug is metabolized to be converted into the active entity, once inside the cell where water-solubility is beneficial.

As used herein, the term "solvate" means a compound of the present invention, which further includes a stoichiometric or non-stoichiometric amount of a solvent bound thereto by non-covalent intermolecular forces. Preferred solvents are volatile, non-toxic, and/or acceptable for administration to humans. Where the solvent is water, the solvate refers to a hydrate.

Unless otherwise specified, the term "compound in accordance with the present invention" is intended to encompass a compound per se, and a pharmaceutically acceptable isomer, prodrug and solvate thereof.

As used herein, the term "alkyl" refers to an aliphatic hydrocarbon group. The alkyl moiety may be a "saturated alkyl" group, which means that it does not contain any alkene or alkyne moieties. Alternatively, the alkyl moiety may also be an "unsaturated alkyl" moiety, which means that it contains at least one alkene or alkyne moiety. The term "alkene" moiety refers to a group in which at least two carbon atoms form at least one carbon-carbon double bond, and an "alkyne" moiety refers to a group in which at least two carbon atoms form at least one carbon-carbon triple bond. The alkyl moiety, regardless of whether it is substituted or unsubstituted, may be branched, linear or cyclic. The alkyl may also have 1 to 20 carbon atoms, may be middle size alkyl which has 1 to 10 carbon atoms, is preferably lower alkyl which has 1 to 6 carbon atoms, for example, $C_1$-$C_4$ alkyl is 1 to 4 carbon atoms in alkyl chain, i.e., alkyl chain is selected from the group consisting methyl, ethyl, propyl, iso-propyl, n-butyl, iso-butyl, sec-butyl and t-butyl.

As used herein, the term "cycloalkyl" is a kind of alkyl which contains 3 to 15 carbon atoms and, if a double bond between carbon atoms is present, the double bond is not alternated or resonant. That may comprise 1 to 4 rings. Examples of unsubstituted cycloalkyl group is cyclopropyl, cyclobutyl, cyclopentyl, cyclohexyl, adamantyl, in case of substituted cycloalkyl group, examples of substituent is selected from the group consisting halogen, alkyl, alkoxy, alkylhydroxy, amino, nitro, cyano, thiol, and/or alkylthio.

As used herein, the term "alkoxy" or "alkylthio" refers to an alkyl group which is each independently bonded via oxygen (—O—) or sulfur (—S—) as described above.

As used herein, the term "heterocycloalkyl" means a carbocyclic group in which one or more ring carbon atoms are substituted with at least any one of oxygen, nitrogen and sulfur, and which may be of an aromatic structure or not so. The heterocycloalkyl includes, for example, but is not limited to furan, thiophene, pyrrole, pyrroline, pyrrolidine, oxazole, thiazole, imidazole, imidazoline, imidazolidine, pyrazole, pyrazoline, pyrazolidine, isothiazole, triazole, thiadiazole, pyran, pyridine, piperidine, morpholine, thiomorpholine, pyridazine, pyrimidine, pyrazine, piperazine and triazine As used herein, the term "aryl" refers to an aromatic substituent group which has at least one ring having a conjugated pi (π) electron system and includes both carbocyclic aryl (for example, phenyl) and heterocyclic aryl (for example, pyridine) groups. This term includes monocyclic or fused-ring polycyclic (i.e., rings which share adjacent pairs of carbon atoms) groups. Aryl group contains at least one ring having at least 6 atoms, and contains less than 5 rings which have less than 22 atoms. Double bonds between carbon atom(s) and/or hetero atom(s) are alternated or resonant. Aryl group may be optionally substituted by at least any one of halogen, alkyl, alkoxy, hydroxy, carboxy, carbamoyl, alkyloxycarbonyl, nitro, trifluoromethyl, amino, cycloalkyl, cyano, alkyl S(O)$_m$ (m=O, 1, 2) and thiol.

As used herein, the term "heteroaryl" refers to an aromatic group that contains at least one heterocyclic ring.

Examples of aryl or heteroaryl include, but are not limited to, phenyl, furan, pyran, pyridyl, pyrimidyl and triazyl.

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ in Formula 1 in accordance with the present invention may be optionally substituted. When substituted, the substituent group(s) is(are) one or more group(s) individually and independently selected from hydrogen, halogen, hydroxy, $C_1$-$C_6$ alkyl, $C_3$-$C_8$ cycloalkyl, $C_4$-$C_{10}$ aryl, $C_4$-$C_{10}$ heteroaryl, heteroalicyclic, $C_1$-$C_6$ alkoxy, aryloxy, mercapto, alkylthio, arylthio, cyano, halogen, carbonyl, thiocarbonyl, O-carbamyl, N carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino including mono and di substituted amino, and protected derivatives thereof.

Among compounds of Formula 1 in accordance with the present invention, preferred are compounds of Formulas 2 and 5 below.

Compounds of Formula 2 below are compounds wherein m is 1, n is 0 and adjacent carbon atoms form a cyclic structure (furan ring) via a direct bond therebetween and are often referred to as 'furanotetrahydrophenanthrene compounds' or 'furanotetrahydro-3,4-phenanthrenequinone' hereinafter.

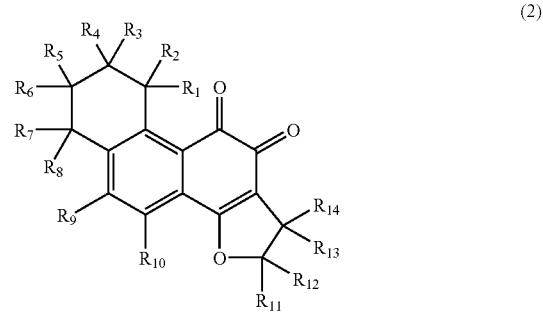

(2)

Compounds of formula 3 below are compounds wherein m and n are 1 respectively and are often referred to as 'pyranotetrahydrophenanthrene compounds' or 'pyranotetrahydro-3,4-phenanthrenequinone' hereinafter.

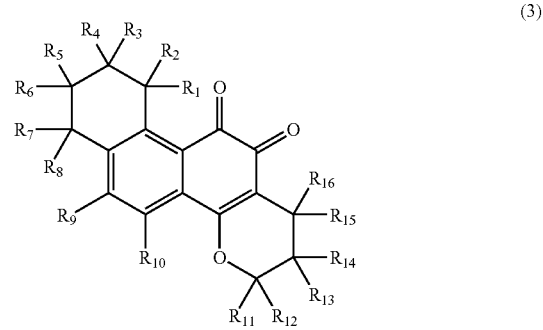

(3)

In the compounds of formula 1, it is also possible that $R_2$ and $R_4$ and/or $R_6$ and $R_8$ form a chemical bond. In this regard, when m and n are respectively 0 and 1, the compounds are classified into two types of formula 4 and formula 5 below.

That is, compounds of Formula 4, wherein m is 1, n is 0 and adjacent carbon atoms form a cyclic structure (furan ring) via a direct bond therebetween, are often referred to as 'furanophenanthrene compounds' or 'furano-3,4-phenanthrenequinone' hereinafter.

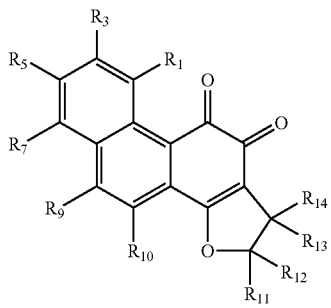

(4)

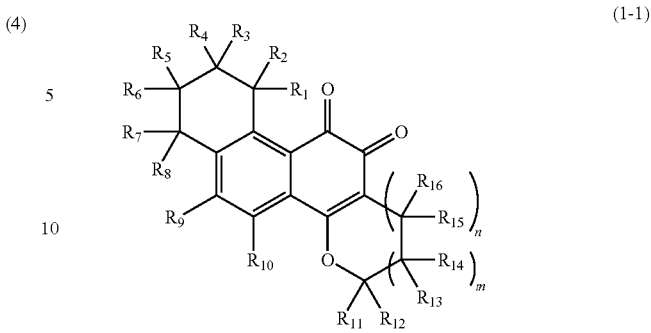

(1-1)

Compounds of Formula 5, wherein m and n are 1 respectively, are often referred to as 'pyranophenanthrene compounds' or 'pyrano-3,4-phenanthrenequinone' hereinafter.

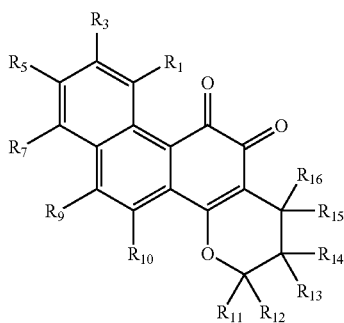

(5)

Among the compounds of Formula 1 in accordance with the present invention, excluded are the compounds that in case that m is 1, n is 0, carbon atoms adjacent to m or n form a cyclic structure via a direct bond, $R_9$, $R_{10}$ and $R_{11}$ are hydrogen, and $R_{12}$ and $R_{13}$ are hydrogen or taken together to form a double bond, (i) when $R_1$ to $R_6$ are hydrogen and $R_7$ and $R_8$ are methyl, $R_{14}$ is methyl, and (ii) when $R_1$, $R_3$ and $R_5$ are hydrogen and $R_2$, $R_4$, $R_6$ and $R_8$ are taken together to form a double bond and $R_7$ is methyl, $R_{14}$ is methyl, because they are naturally occurring tanshinone derivatives.

In one preferred embodiment, the compound of Formula 1 is a compound wherein $R_1$, $R_2$, $R_3$, $R_4$, $R_5$, $R_6$, $R_7$ and $R_8$ are each independently selected from the group consisting hydrogen, halogen, $C_1$-$C_6$ alkyl and $C_1$-$C_6$ alkyloxy, or two substituents thereof are taken together to form a double bond, and $R_9$, $R_{10}$ $R_{11}$, $R_{12}$, $R_{13}$, $R_{14}$, $R_{15}$ and $R_{16}$ are each independently hydrogen or $C_1$-$C_6$ alkyl.

In accordance with another aspect of the present invention, there is provided a novel compound represented by Formula 1-1, or an isomer, prodrug, or solvate thereof.

wherein $R_1$, $R_2$, $R_3$, $R_4$, $R_5$, $R_6$, $R_7$ and $R_8$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl, or heterocycloalkyl, $C_4$-$C_{10}$ aryl or heteroaryl, or two substituents thereof may be taken together to form a cyclic structure or form a double bond;

$R_9$ and $R_{10}$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl, or heterocycloalkyl, $C_4$-$C_{10}$ aryl or heteroaryl;

$R_{11}$, $R_{12}$, $R_{13}$, $R_{14}$, $R_{15}$ and $R_{16}$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl or heterocycloalkyl, $C_4$-$C_{10}$ aryl or heteroaryl, or two substituents thereof may be taken together to form a cyclic structure or form a double bond;

m and n are each independently 0 or 1, when m or n is 0, carbon atoms adjacent to m or n may form a cyclic structure via a direct bond;

in the condition that m is 1, n is 0, carbon atoms adjacent to m or n form a cyclic structure via a direct bond, and $R_9$ and $R_{10}$ are hydrogen, (i) when $R_1$ to $R_6$ are hydrogen and $R_7$ and $R_8$ are methyl, if $R_{12}$ and $R_{13}$ is hydrogen, then $R_{11}$ or $R_{14}$ is not methyl, and if $R_{12}$ and $R_{13}$ form a double bond, then $R_{14}$ is not methyl, (ii) when $R_1$, $R_3$ and $R_5$ are hydrogen, and $R_2$, $R_4$, $R_6$ and $R_8$ are taken together to form a double bond, if $R_7$ is methyl and $R_{12}$ and $R_{13}$ are hydrogen, then $R_{14}$ is not methyl, and if $R_7$ is hydrogen and $R_{12}$ and $R_{13}$ are hydrogen, then $R_{11}$ is not methyl, and if $R_7$ is methyl and $R_{12}$ and $R_{13}$ form a double bond, then $R_{14}$ is not methyl.

In one preferred embodiment, the compound of Formula 1-1 is a compound wherein $R_1$, $R_2$, $R_3$, $R_4$, $R_5$, $R_6$, $R_7$ and $R_8$ are each independently selected from the group consisting hydrogen, halogen, $C_1$-$C_6$ alkyl and $C_1$-$C_6$ alkyloxy, or two substituents thereof may be taken together to form a double bond, and $R_9$, $R_{10}$ $R_{11}$, $R_{12}$, $R_{13}$, $R_{14}$, $R_{15}$ and $R_{16}$ may be each independently hydrogen or $C_1$-$C_6$ alkyl.

Unless otherwise specified, the term "the compound of Formula 1-1" is intended to encompass a compound per se, and a pharmaceutically acceptable isomer, prodrug, and solvate thereof.

The present inventors have confirmed that the novel compound of Formula 1-1 has therapeutic effects on metabolic syndrome, as will be illustrated in Experimental Examples hereinafter, and have measured activity of the compound of Formula 1-1 on AMPK activity in myoblast cells (C2C12) and suppression of cellular differentiation in preadipocytes (3T3-L1 and F442A cells) and as a result, have confirmed that such a compound exhibits superior AMPK activation effects and inhibitory effects of adipocyte differentiation.

Below, the compound of Formula 1 or Formula 1-1 in accordance with the present invention, as will be illustrated hereinafter, can be prepared.

In general, tricyclic naphthoquinone (pyrano-o-naphthoquinone and furano-o-naphthoquinone) derivatives can be synthesized mainly by two methods. One is to derive cyclization reaction using 3-allyl-2-hydroxy-1,4-naphthoquinone in acid catalyst condition, like in the following β-lapachone synthesis method. In the present invention, in the case of a compound in which $R_{11}$ and $R_{12}$ are not hydrogen simultaneously, most of compounds of formula 1 were synthesized on the basis of that method.

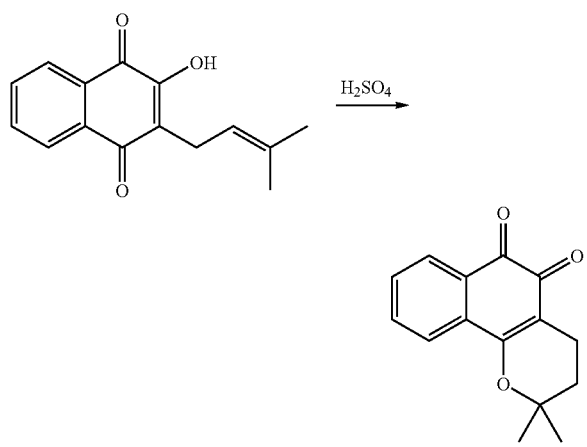

That is, 3-allyloxy-1,4-phenanthrenequinone can be obtained by deriving Diels-Alder reaction between 2-allyloxy-1,4-benzoquinone and styrene or 1-vinylcyclohexane derivatives and dehydrating the resulting intermediates using oxygen present in the air or oxidants such as NaIO4 and DDQ. By further re-heating the above compound, 2-allyl-3-hydroxy-1,4-phenanthrenequinone of Lapachole form can be synthesized via Claisen rearrangement.

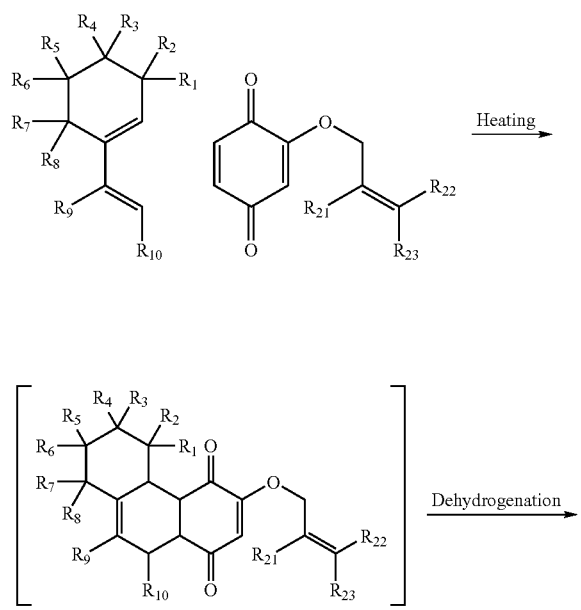

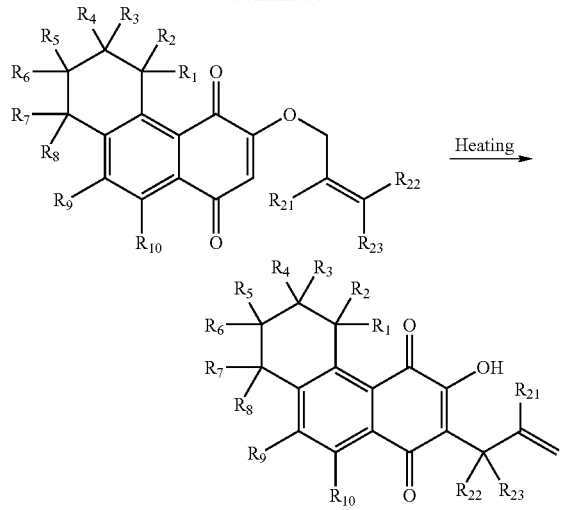

When the thus obtained 2-allyl-3-hydroxy-1,4-phenanthrenequinone is ultimately subject to cyclization in an acid catalyst condition, various 3,4-phenanthrenequinone-based or 5,6,7,8-tetrahydro-3,4-phenanthrenequinone-based compounds can be synthesized. In this case, 5 or 6-cyclic cyclization occurs depending on the types of substituents ($R_{21}$, $R_{22}$, $R_{23}$ in the above formula) and also they are converted to the corresponding, adequate substituents ($R_{11}$, $R_{12}$, $R_{13}$, $R_{14}$, $R_{15}$, $R_{16}$).

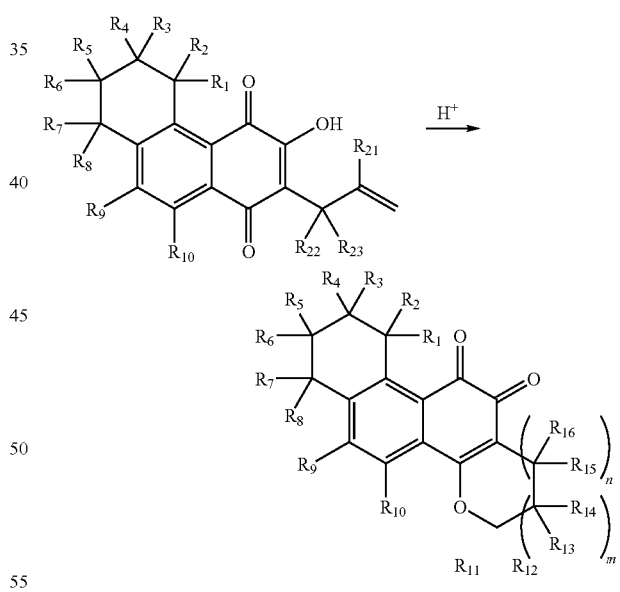

Further, 3-allyloxy-1,4-phenanthrenequinone is hydrolyzed to 3-oxy-1,4-phenanthrenequinone, in the condition of acid ($H^+$) or alkali ($OH^-$) catalyst, which is then reacted with various allyl halides to synthesize 2-allyl-3-hydroxy-1,4-phenanthrenequinone by C-alkylation. The thus obtained 2-allyl-3-hydroxy-1,4-phenanthrenequinone derivatives are subject to cyclization in the condition of acid catalyst to synthesize various 3,4-phenanthrenequinone-based or 5,6,7,8-tetrahydro-3,4-naphthoquinone-based compounds. In this case, 5 or 6-cyclic cyclization occurs depending on the types of substituents ($R_{21}$, $R_{22}$, $R_{23}$, $R_{24}$ in the above formula), and also they are converted to the corresponding, adequate substituents ($R_{11}$, $R_{12}$, $R_{13}$, $R_{14}$, $R_{15}$, $R_{16}$).

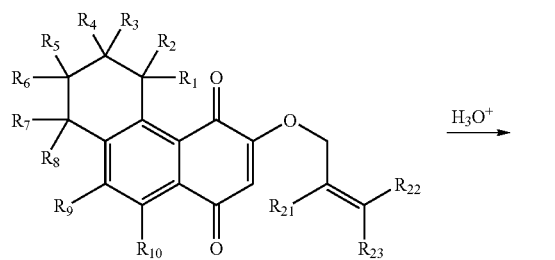

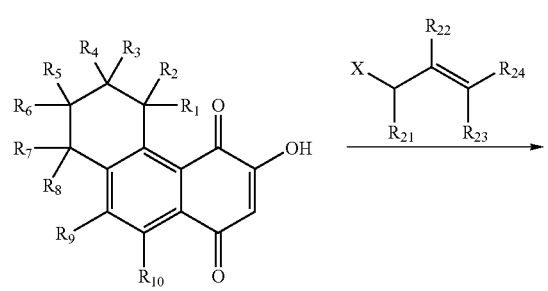

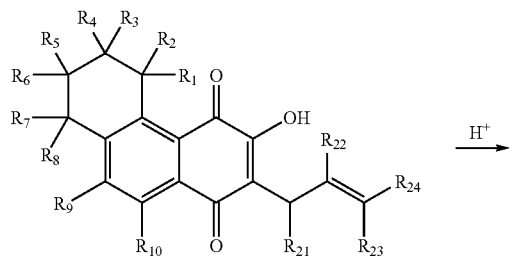

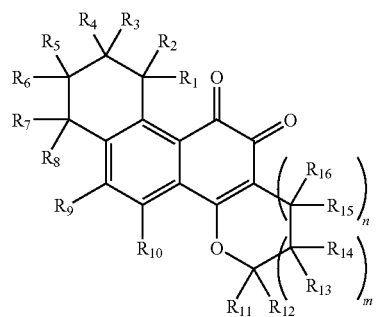

However, compounds in which substituents $R_{11}$ and $R_{12}$ are hydrogen simultaneously cannot be obtained by cyclization in the condition of acid catalyst. These compound were obtained on the basis of the method reported by J. K. Snyder (Tetrahedron Letters, 28, 3427~3430, 1987; Journal of Organic Chemistry, 55, 4995~5008, 1990), more specifically, by first obtaining furanobenzoquinone, to which a furan ring is introduced, by cyclization, and then obtaining tricyclic phenanthroquinone by cyclization with 1-vinylcyclohexene derivative, followed by reduction via hydrogen addition. The above synthesis process can be summarized as follows.

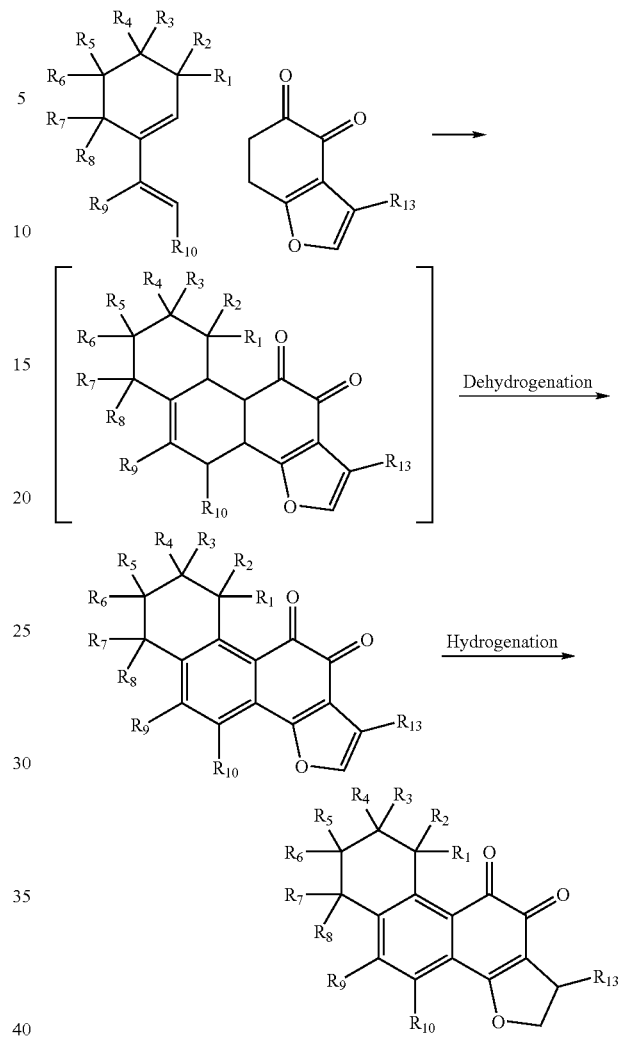

Based on the above-mentioned preparation methods, various derivatives may be synthesized using relevant synthesis methods, depending upon kinds of substituents.

Among the compound of Formula 1 or Formula 1-1 in accordance with the present invention, particularly preferred compounds are exemplified in Table 1 below, but are not limited to. The specific preparation methods will be described in the following Examples.

TABLE 1

| No. | Chemical structure | Formula | Molecular weight |
| --- | --- | --- | --- |
| 1 | 2-Methyl-1,2,6,7,8,9-hexahydro-phenanthro[1,2-b]furan-10,11-dione | $C_{17}H_{16}O_3$ | 268.31 |
| 2 | 2,6,6-Trimethyl-1,2,6,7,8,9-hexahydro-phenanthro[1,2-b]furan-10,11-dione | $C_{19}H_{20}O_3$ | 296.36 |
| 3 | 2,6,6-Trimethyl-1,2,6,7,8,9-hexahydro-phenanthro[1,2-b]furan-10,11-dione | $C_{19}H_{20}O_3$ | 296.36 |
| 4 | 1,1,2,6,6-Pentamethyl-1,2,6,7,8,9-hexahydro-phenanthro[1,2-b]furan-10,11-dione | $C_{21}H_{24}O_3$ | 324.41 |
| 5 | 1,2,2,6,6-Pentamethyl-1,2,6,7,8,9-hexahydro-phenanthro[1,2-b]furan-10,11-dione | $C_{21}H_{24}O_3$ | 324.41 |
| 6 | 3,3-Dimethyl-2,3,7,8,9,10-hexahydro-1H-4-oxa-chrysene-11,12-dione | $C_{19}H_{20}O_3$ | 296.36 |

TABLE 1-continued

| No. | Chemical structure | Formula | Molecular weight |
|---|---|---|---|
| 7 | 2-Methyl-1,2-dihydro-phenanthro[1,2-b]furan-10,11-dione | $C_{17}H_{12}O_3$ | 264.28 |
| 8 | 1,1,2-Trimethyl-1,2-dihydro-phenanthro[1,2-b]furan-10,11-dione | $C_{19}H_{16}O_3$ | 292.33 |
| 9 | 2,5-Dimethyl-1,2-dihydro-phenanthro[1,2-b]furan-10,11-dione | $C_{18}H_{14}O_3$ | 278.30 |
| 10 | 1,1,2,5-Tetramethyl-1,2-dihydro-phenanthro[1,2-b]furan-10,11-dione | $C_{20}H_{18}O_3$ | 306.36 |
| 11 | 8-tert-Butyl-2-methyl-1,2-dihydro-phenanthro[1,2-b]furan-10,11-dione | $C_{21}H_{20}O_3$ | 320.38 |
| 12 | 8-tert-Butyl-1,1,2-trimethyl-1,2-dihydro-phenanthro[1,2-b]furan-10,11-dione | $C_{23}H_{24}O_3$ | 348.43 |
| 13 | 8-Chloro-2-methyl-1,2-dihydro-phenanthro[1,2-b]furan-10,11-dione | $C_{17}H_{11}ClO_3$ | 298.72 |
| 14 | 2,8-Dimethyl-1,2-dihydro-phenanthro[1,2-b]furan-10,11-dione | $C_{18}H_{14}O_3$ | 278.30 |
| 15 | 8-Methoxy-2-methyl-1,2-dihydro-phenanthro[1,2-b]furan-10,11-dione | $C_{18}H_{14}O_4$ | 294.30 |
| 16 | 3,3,6-Trimethyl-2,3-dihydro-1H-4-oxa-chrysene-11,12-dione | $C_{20}H_{18}O_3$ | 306.36 |

The term "pharmaceutical composition" as used herein means a mixture of a compound of Formula I with other chemical components, such as diluents or carriers. The pharmaceutical composition facilitates administration of the compound to an organism. Various techniques of administering a compound are known in the art and include, but are not limited to oral, injection, aerosol, parenteral and topical administrations. Pharmaceutical compositions can also be obtained by reacting compounds of interest with acids such as hydrochloric acid, hydrobromic acid, sulfuric acid, nitric acid, phosphoric acid, methanesulfonic acid, p-toluenesulfonic acid, salicylic acid and the like.

The term "therapeutically effective amount" means an amount of an active ingredient that is effective to relieve or reduce to some extent one or more of the symptoms of the disease in need of treatment, or to retard initiation of clinical markers or symptoms of a disease in need of prevention, when the compound is administered. Thus, a therapeutically effective amount refers to an amount of the active ingredient which exhibit effects of (i) reversing the rate of progress of a disease; (ii) inhibiting to some extent further progress of the disease; and/or, (iii) relieving to some extent (or, preferably, eliminating) one or more symptoms associated with the disease. The therapeutically effective amount may be empirically determined by experimenting with the compounds concerned in known in vivo and in vitro model systems for a disease in need of treatment.

The pharmaceutical composition of the present invention may be manufactured in a manner that is itself known, e.g., by means of conventional mixing, dissolving, granulating, dragee-making, levigating, emulsifying, encapsulating, entrapping or lyophilizing processes.

Thus, pharmaceutical compositions for use in accordance with the present invention may include pharmaceutically acceptable carriers, diluents, excipients or any combination thereof additionally. That is, may be formulated in a conventional manner using one or more pharmaceutically acceptable carriers comprising excipients and auxiliaries which facilitate processing of the active compounds into preparations which can be used pharmaceutically. The pharmaceutical composition facilitates administration of the compound to an organism.

The term "carrier" means a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffer solution is phosphate buffered saline (PBS) because it mimics the ionic strength conditions of human body fluid. Since buffer salts can control the pH of a solution at low concentrations, a buffer diluent rarely modifies the biological activity of a compound.

The compounds described herein may be administered to a human patient per se, or in the form of pharmaceutical compositions in which they are mixed with other active ingredients, as in combination therapy, or suitable carriers or excipient(s). Proper formulation is dependent upon the route of administration chosen. Techniques for formulation and administration of the compounds may be found in "Remington's Pharmaceutical Sciences," Mack Publishing Co., Easton, Pa., 18th edition, 1990.

In order to administering an active ingredient to the body, various techniques which are pharmaceutical formulation, are known in the art, and include, but are not limited to oral, injection, aerosol, parenteral and topical administrations. Alternatively, it can also be obtained by reacting compounds of interest with acids such as hydrochloric acid, hydrobromic acid, sulfuric acid, nitric acid, phosphoric acid, methanesulfonic acid, p-toluenesulfonic acid, salicylic acid and the like.

The pharmaceutical formulation can be carried out by a conventional method known in the art. Preferably, it may be pharmaceutically acceptable oral, external use, transdermal, transmucosal, or formulation of injection, and more preferably it may be an oral formulation.

Pharmaceutical compositions suitable for use in the present invention include compositions in which the active ingredients are contained in an amount effective to achieve its intended purpose. Specifically, a therapeutically effective amount means an amount of compound effective to prevent, alleviate or ameliorate symptoms of disease. Determination of a therapeutically effective amount is well within the capability of those skilled in the art, especially in light of the detailed disclosure provided herein.

The compound of Formula 1 or Formula 1-1 in accordance with the present invention, as defined in this disclosure, may be particularly effective for use in the treatment and prevention of disease involving metabolic syndromes, thus the present invention provides a use of a compound of Formula 1 or Formula 1-1 in the preparation of a drug for the treatment or prevention of metabolic syndromes.

In accordance with another aspect of the present invention, there is provided a use of the pharmaceutical compositions as a drug for the treatment or prevention of disease syndromes, and methods of treating the disease involving metabolic syndromes by administering the pharmaceutical compositions to the patient.

Examples of the disease involving metabolic syndromes include, but are not limited to, obesity, liver diseases, arteriosclerosis, cerebral apoplexy, myocardial infarction, ischemic diseases, diabetes, diabetes-related complications and inflammatory diseases. Diabetic complications include, for example hyperlipidemia, hypertension, retinopathy, renal insufficiency, and the like. The term "treatment" refers to stopping or delaying of the disease progress, when the drug is used in the subject exhibiting symptoms of disease onset. The term "prevention" refers to stopping or delaying of symptoms of disease onset, when the drug is used in the subject exhibiting no symptoms of disease onset but having high risk of disease onset.

DETAILED DESCRIPTION OF PREFERRED EMBODIMENTS

Figure 1:
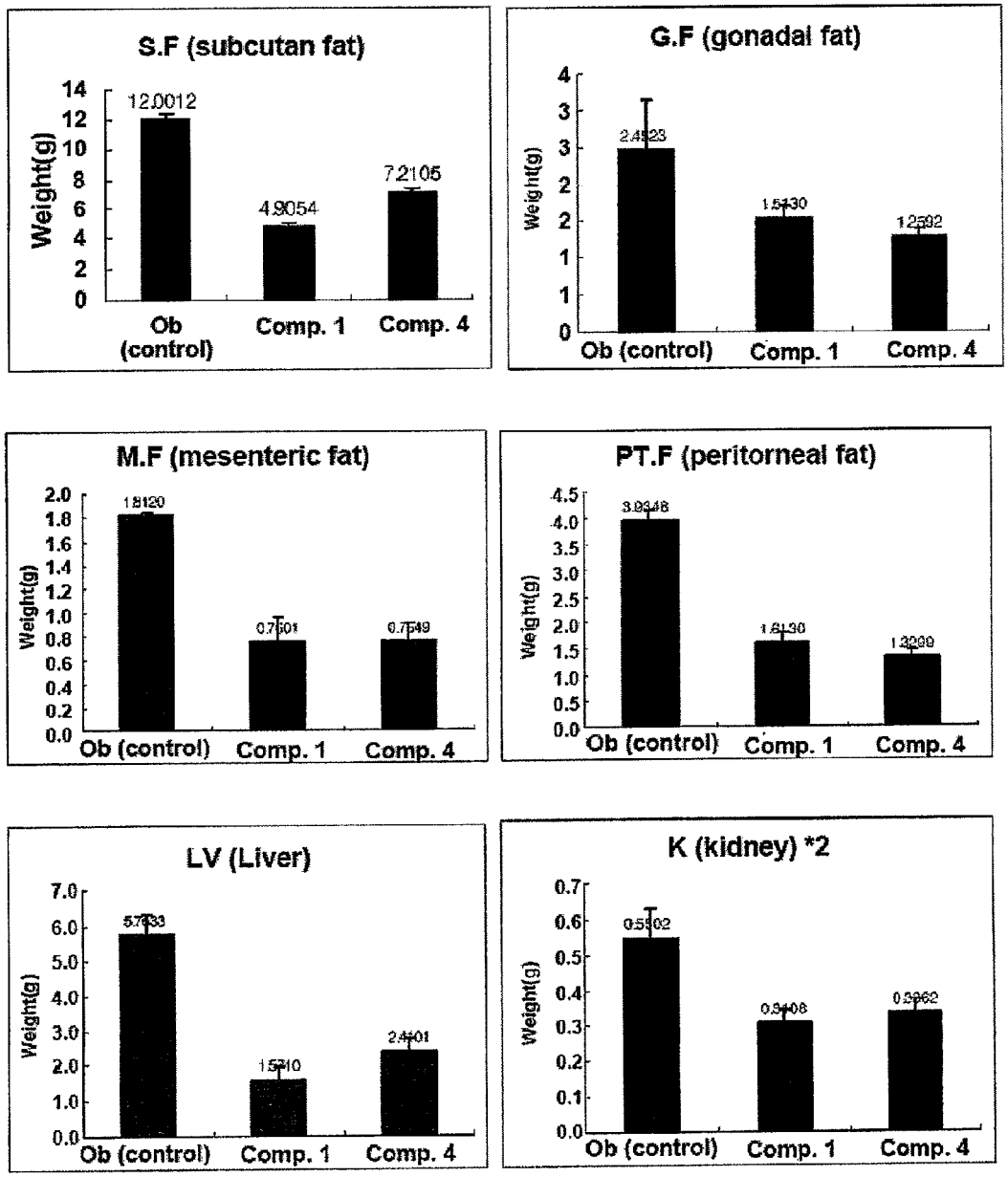
FIGS. 1 through 3 are graphs showing fat distribution in terms of numerical values according to each organ of C57BL/6JL Lep ob/Lep ob mice which were administered with a pharmaceutical composition in accordance with the present invention.

Now, the present invention will be described in more detail with reference to the following Examples and Experimental Examples. These examples are provided only for illustrating the present invention and should not be construed as limiting the scope and spirit of the present invention.

Example 1

Synthesis of Compound 1

2-Allyloxy-1,4-benzoquinone (10.0 g, 60.9 mM) and 1-Vinylcyclohexene (19.8 g, 183 mM) were dissolved in 100 ml of MeOH, and refluxed for 3 hours. The reaction solution was cooled to room temperature, and then Triethylamine (5 ml) and $NaIO_4$ (13.0 g, 61.0 mM) were added thereto, and stirred vigorously for another 1 hours. Reaction solution therein was filtered and the filtrate was concentrated by distillation under reduced pressure and was then purified by chromatography on silica gel to give 7.6 g (28.4 mM) of 3-Allyloxy-5,6,7,8-tetrahydro-1,4-phenanthrenequinone.

$^1$H-NMR ($CDCl_3$): δ 7.91 (1H, d, J=7.9 Hz), 7.42 (1H, d, J=7.9 Hz), 6.07 (1H, s), 6.05 (1H, m), 5.48 (1H, d, J=17.2 Hz), 5.39 (1H, d, J=10.5 Hz), 4.56 (2H, d, J=5.5 Hz), 3.27 (2H, t, J=5.1 Hz), 2.89 (2H, t, J=6.2 Hz), 1.82 (4H, m).

$^{13}$C-NMR ($CDCl_3$): δ 185.307, 181.947, 159.638, 144.852, 141.398, 134.881, 131.654, 130.626, 128.674, 123.903, 119.819, 108.777, 69.963, 31.084, 28.829, 23.048, 21.816.

Mass (m/z): 268(95), 227(100), 157(91).

The thus-obtained 3-Allyloxy-5,6,7,8-tetrahydro-1,4-phenanthrenequinone was dissolved in 50 ml of toluene and refluxed for 5 hours and then was concentrated by distillation under reduced pressure and was then purified by chromatography on silica gel to give 7.3 g (27.2 mM) of 2-Allyl-3-hydroxy-5,6,7,8-tetrahydro-1,4-phenanthrenequinone.

$^1$H-NMR ($CDCl_3$): δ 7.96 (1H, d, J=7.9 Hz), 7.65 (1H, s), 7.43 (1H, d, J=7.9 Hz), 5.9 (1H, m), 5.15 (1H, d, J=17.1 Hz), 5.03 (1H, d, J=10.0 Hz), 3.33 (2H, d, J=6.5 Hz), 3.27 (2H, t, J=5.9 Hz), 2.88 (2H, t, J=6.2 Hz), 1.83 (4H, m).

$^{13}$C-NMR ($CDCl_3$): δ 184.531, 183.081, 153.505, 144.257, 141.520, 135.625, 134.023, 132.610, 126.626, 124.684, 119.226, 116.045, 30.891, 28.876, 27.360, 22.916, 21.782.

Mass (m/z): 268(100), 253(28), 240(30), 225(24).

The thus-obtained 2-Allyl-3-hydroxy-5,6,7,8-tetrahydro-1,4-phenanthrenequinone was then mixed with 10 ml of sulfuric acid, without further purification, the resulting mixture was stirred vigorously at room temperature for 10 min and 50 g of ice was added thereto to complete the reaction. 20 ml of $CH_2Cl_2$ was added to the reaction materials which were shaken vigorously. Thereafter, a $CH_2Cl_2$ layer was separated and washed with 5% $NaHCO_3$. An aqueous layer was extracted once again using 10 ml of $CH_2Cl_2$, and combined with the previously extracted organic layer. The organic layer was dried over $MgSO_4$, concentrated to give impure Compound 1. The thus-obtained Compound 1 first purified by chromatography on silica gel, and then the thus-obtained Compound 1 was recrystallized from isopropanol, thereby obtaining 4.6 g (17.2 mM) of pure Compound 1.

$^1$H-NMR ($CDCl_3$): δ 7.44 (1H, d, J=7.8 Hz), 7.32 (1H, d, J=7.8 Hz), 5.23 (1H, m), 3.23 (3H, m), 2.85 (2H, t, J=7.1 Hz), 2.71 (1H, dd, J=15.1, 7.1 Hz), 1.80 (4H, m), 1.56 (3H, d, J=6.4 Hz).

$^{13}$C-NMR ($CDCl_3$): δ 184.074, 175.620, 170.783, 144.303, 143.766, 134.635, 128.293, 126.586, 122.217, 113.258, 84.182, 33.394, 30.942, 28.545, 22.836, 21.993, 21.842.

Mass (m/z): 268(192), 240(100), 225(27), 211(24).

Example 2

Synthesis of Compound 2

2-Allyloxy-1,4-benzoquinone (10.0 g, 60.9 mM) and 6,6-Dimethyl-1-Vinylcyclohexene (19.8 g, 183 mM) were dissolved in 100 ml of MeOH, and refluxed for 3 hours. 3-Allyloxy-8,8-dimethyl-5,6,7,8-tetrahydro-1,4-phenanthrenequinone (6.5 g, 22.0 mM) was obtained in the same manner as in Example 1.

$^1$H-NMR ($CDCl_3$): δ 7.95 (1H, d, J=8.2 Hz), 7.72 (1H, d, J=8.2 Hz), 6.06 (1H, s), 6.05 (1H, m), 5.48 (1H, d, J=17.3 Hz), 5.39 (1H, d, J=10.5 Hz), 4.56 (2H, d, J=5.5 Hz), 3.24 (2H, t, J=6.2 Hz), 1.81 (2H, m), 1.67 (2H, m), 1.32 (6H, s).

$^{13}$C-NMR ($CDCl_3$): δ 185.114, 181.840, 159.803, 153.329, 140.709, 132.589, 131.328, 130.623, 128.652, 124.101, 119.713, 108.629, 69.915, 37.785, 34.911, 31.837, 29.921, 19.247.

2-Allyl-3-hydroxy-8,8-dimethyl-5,6,7,8-tetrahydro-1,4-phenanthrenequinone was obtained in the same manner as in Example 1.

$^1$H-NMR ($CDCl_3$): δ 8.00 (1H, d, J=7.9 Hz), 7.74 (1H, d, J=7.9 Hz), 7.71 (1H, s), 5.89 (1H, m), 5.41 (1H, dd, J=17.1, 1.6 Hz), 5.02 (1H, dd, J=9.9, 1.5 Hz), 3.31 (2H, dt, J=6.5, 1.5 Hz), 3.25 (2H, t, J=6.3 Hz), 1.82 (2H, m), 1.68 (2H, m), 1.32 (6H, s).

$^{13}$C-NMR ($CDCl_3$): δ 184.320, 182.952, 153.611, 152.757, 140.881, 133.974, 133.323, 132.297, 126.463, 124.904, 119.113, 115.975, 37.631, 34.755, 31.709, 29.866, 27.273, 19.050.

From the thus-obtained 2-Allyl-3-hydroxy-8,8-dimethyl-5,6,7,8-tetrahydro-1,4-phenanthrenequinone, Compound 2 was obtained in the same manner as in Example 1.

$^1$H-NMR ($CDCl_3$): δ 7.63 (1H, d, J=7.8 Hz), 7.50 (1H, d, J=7.8 Hz), 5.22 (1H, m), 3.25 (3H, dd, J=15.1, 9.7 Hz), 2.71 (1H, dd, J=15.1, 7.1 Hz), 1.80 (2H, m), 1.67 (2H, m), 1.55 (3H, d, J=6.4 Hz), 1.32 (3H, s), 1.31 (3H, s).

$^{13}$C-NMR ($CDCl_3$): δ 184.132, 175.798, 170.649, 152.399, 143.687, 132.502, 128.365, 126.349, 122.503, 113.332, 84.160, 37.762, 34.826, 33.363, 31.909, 31.853, 29.655, 21.999, 19.041.

Mass (m/z): 296(95), 282(15), 268(58), 253(100).

Example 3

Synthesis of Compound 3

2-Prenyloxy-1,4-benzoquinone (3.0 g, 15.6 mM) and 1-Vinylcyclohexene (6.75 g, 62.5 mM) were dissolved in 50 ml of MeOH, and refluxed for 3 hours. 3-Prenyloxy-5,6,7,8-tetrahydro-1,4-phenanthrenequinone (1.61 g, 5.44 mM) was obtained in the same manner as in Example 1.

$^1$H-NMR (CDCl$_3$): δ 7.91 (1H, d, J=7.9 Hz), 7.4 (1H, d, J=7.9 Hz), 6.07 (1H, s), 5.50 (1H, t, J=6.8 Hz), 4.54 (2H, d, J=6.8 Hz), 3.26 (2H, t, J=5.9 Hz), 2.88 (2H, t, J=4.7 Hz), 1.82 (4H, m), 1.80 (3H, s), 1.75 (3H, s).

$^{13}$C-NMR (CDCl$_3$): δ 185.414, 182.152, 160.040, 144.722, 141.333, 140.283, 134.809, 131.716, 128.719, 123.852, 117.322, 108.412, 66.280, 31.072, 28.785, 25.811, 23.065, 21.826, 18.317.

Mass (m/z): 296(73), 281(53), 253(18), 228(100), 213(24).

2-((3-Methyl-1-buten)-3-yl)-3-hydroxy-5,6,7,8-tetrahydro-1,4-phenanthrenequinone was obtained in the same manner as in the Example 1.

$^1$H-NMR (CDCl$_3$): δ 8.16 (1H, s), 7.87 (1H, d, J=7.9 Hz), 7.42 (1H, d, J=7.9 Hz), 6.27 (1H, dd, J=17.5, 10.5 Hz), 4.99 (1H, d, J=17.5 Hz), 4.95 (1H, d, J=10.5 Hz), 3.24 (2H, t, J=5.9 Hz), 2.86 (2H, t, J=6.2 Hz), 1.83 (4H, m), 1.54 (6H, s).

$^{13}$C-NMR (CDCl$_3$): δ 185.047, 183.480, 153.102, 148.177, 143.616, 140.918, 135.846, 133.972, 125.986, 125.826, 124.715, 109.250, 40.596, 30.752, 28.813, 27.976, 22.904, 21.825.

Mass (m/z): 296(100), 281(91), 253(24).

From the thus-obtained 24(3-Methyl-1-buten)-3-yl)-3-hydroxy-5,6,7,8-tetrahydro-1,4-phenanthrenequinone, Compound 3 was obtained in the same manner as in Example 1.

$^1$H-NMR (CDCl$_3$): δ 7.64 (1H, d, J=7.8 Hz), 7.32 (1H, d, J=7.8 Hz), 4.63 (1H, q, J=6.6 Hz), 3.21 (2H, t, J=4.8 Hz), 2.84 (1H, t, J=4.2 Hz), 1.79 (4H, m), 1.45 (3H, d, J=6.6 Hz), 1.43 (3H, s), 1.24 (3H, s).

$^{13}$C-NMR (CDCl$_3$): δ 184.450, 175.599, 169.171, 144.072, 143.353, 134.608, 128.443, 126.817, 122.113, 121.512, 92.524, 43.944, 30.894, 28.544, 25.713, 22.850, 21.875, 20.347, 14.548.

Mass (m/z): 296(38), 281(12), 268(44), 253(100).

Example 4

Synthesis of Compound 4

2-Prenyloxy-1,4-benzoquinone (20.0 g, 0.104 M) and 6,6-Dimethyl-1-vinylcyclohexene (56.7 g, 0.416 M) were dissolved in 150 ml of MeOH, and refluxed for 3 hours. 3-Prenyloxy-8,8-dimethyl-5,6,7,8-tetrahydro-1,4-phenanthrenequinone (12.0 g, 0.037 M) was obtained in the same manner as in Example 1.

$^1$H-NMR (CDCl$_3$): δ 7.95 (1H, d, J=8.2 Hz), 7.72 (1H, d, J=8.2 Hz), 6.06 (1H, s), 5.48 (1H, m), 4.54 (2H, d, J=6.8 Hz), 3.24 (2H, t, J=6.2 Hz), 1.81 (2H, m), 1.80 (3H, s), 1.75 (3H, s), 1.67 (2H, m), 1.32 (6H, s).

$^{13}$C-NMR (CDCl$_3$): δ 185.263, 182.095, 160.244, 153.237, 140.677, 140.214, 132.546, 131.425, 128.740, 124.082, 117.354, 108.292, 66.278, 37.830, 34.914, 31.866, 29.909, 25.783, 19.289, 18.296.

2-((3-Methyl-1-buten)-3-yl)-3-hydroxy-5,6,7,8-tetrahydro-1,4-phenanthrenequinone was obtained in the same manner as in Example 1.

$^1$H-NMR (CDCl$_3$): δ 8.18 (1H, s), 7.93 (1H, d, J=8.2 Hz), 7.73 (1H, d, J=8.2 Hz), 6.27 (1H, dd, J=17.5, 10.5 Hz), 4.98 (1H, d, J=17.5 Hz), 4.94 (1H, d, J=10.5 Hz), 3.24 (2H, t, J=6.4 Hz), 1.84 (2H, m), 1.67 (2H, m), 1.54 (6H, s), 1.31 (6H, s).

$^{13}$C-NMR (CDCl$_3$): δ 184.950, 183.386, 153.217, 152.196, 148.152, 140.353, 133.694, 133.607, 125.895, 125.679, 125.001, 109.233, 40.538, 37.667, 34.686, 31.695, 29.851, 27.940, 19.062.

From the thus-obtained 2-((3-Methyl-1-buten)-3-yl)-3-hydroxy-5,6,7,8-tetrahydro-1,4-phenanthrenequinone, Compound 4 was obtained in the same manner as in Example 1.

$^1$H-NMR (CDCl$_3$): δ 7.63 (1H, d, J=8.1 Hz), 7.50 (1H, d, J=8.1 Hz), 4.63 (1H, q, J=6.6 Hz), 3.21 (2H, t, J=6.3 Hz), 1.78 (2H, m), 1.65 (2H, m), 1.45 (3H, d, J=6.6 Hz), 1.42 (3H, s), 1.31 (3H, s), 1.30 (3H, s), 1.24 (3H, s).

$^{13}$C-NMR (CDCl$_3$): δ 184.480, 175.733, 168.973, 151.951, 143.368, 132.422, 128.488, 126.555, 122.389, 121.566, 92.501, 43.902, 37.764, 34.728, 31.865, 31.817, 29.605, 25.715, 20.289, 19.016, 14.541.

Example 5

Synthesis of Compound 5

In the process of synthesizing compound 4 in Example 4, a little amount of compound 5(~10%) is obtained as an isomer of compound 4. Therefore, when Compound 4 was purified by chromatography on silica gel, Compound 5 was obtained together.

$^1$H-NMR (CDCl$_3$): δ 7.62 (1H, d, J=8.1 Hz), 7.50 (1H, d, J=8.1 Hz), 3.22 (2H, t, J=6.3 Hz), 3.17 (1H, q, J=7.1 Hz), 1.78 (2H, m), 1.65 (2H, m), 1.50 (3H, s), 1.47 (3H, s), 1.31 (6H, s), 1.24 (3H, d, J=7.1 Hz).

$^{13}$C-NMR (CDCl$_3$): δ 184.375, 175.939, 168.670, 152.055, 143.363, 132.393, 128.454, 126.612, 122.511, 118.083, 94.808, 43.816, 37.701, 34.704, 31.823, 29.608, 28.780, 22.263, 18.988, 14.132.

Example 6

Synthesis of Compound 6

A solution which obtained 3-Allyloxy-5,6,7,8-tetrahydro-1,4-phenanthrenequinone (10.0 g, 37.0 mM) in Example 1 was dissolved in 100 ml of MeOH, was stirred at room temperature, concentrated sulfuric acid was gradually added thereto, and then was additionally stirred for another 1 hour, neutralize solution by 100 ml of saturated aqueous solution was added to the reaction solution, and then 100 ml of CH$_2$Cl$_2$ was added to the solution which was then shaken vigorously Thereafter, a organic layer was separated. The organic layer was dried over MgSO$_4$ and concentrated and purified by chromatography on silica gel to give 8.4 g (36.8 mM) of 3-Hydroxy-5,6,7,8-tetrahydro-1,4-phenanthrenequinone.

$^1$H-NMR (CDCl$_3$): δ 7.94 (1H, d, J=8.0 Hz), 7.62 (1H, s), 7.47 (1H, d, J=8.0 Hz), 6.27 (1H, s), 3.28 (2H, t, J=6.0 Hz), 2.89 (2H, t, J=6.0 Hz), 1.84 (4H, m).

3-Hydroxy-5,6,7,8-tetrahydro-1,4-phenanthrenequinone (8.4 g, 37 mM) was dissolved in 70 ml of DMSO, and 560 g (75 mM) of LiH was gradually added thereto. The reaction solution was stirred, and after confirming no further production of hydrogen, was additionally stirred for another 30 min. Then, 12.0 g (80 mM) of prenyl bromide (1-bromo-3-methyl-2-butene) and 3.35 g (0.025 M) of LiI were gradually added thereto. The reaction solution was heated to 45° C. and then stirred vigorously for 12 hours at that temperature. The reaction solution was cooled below 10° C., and 100 ml of cold water was first added. Thereafter, 1N HCl was gradually added to maintain the resulting solution at an acidic pH>3. 200 ml of EtOAc was added to the reaction mixture which was then shaken vigorously thereafter, an organic layer was separated. The organic layer was washed with 100 ml of 5% NaHCO$_3$, and was concentrated. The resulting concentrates purified by chromatography on silica gel to give 1.81 g (4.9 mM) of 2-Prenyl-3-prenyloxy-5,6,7,8-tetrahydro-1,4- phenanthrenequinone. The resulting was mixed with 5 ml of sulfuric acid, and the mixture was vigorously stirred at room temperature for 10 min and 20 g of ice was added thereto to complete the reaction. 60 ml of $CH_2Cl_2$ was added to the reaction materials which were then shaken vigorously. Thereafter, a $CH_2Cl_2$ layer was separated and washed with 5% $NaHCO_3$. An aqueous layer was extracted once again using 10 ml of $CH_2Cl_2$, washed with 5% $NaHCO_3$ and combined with the previously extracted organic layer. The organic layer was concentrated $MgSO_4$ and the resulting concentrates purified by chromatography on silica gel to give 0.83 g (2.8 mM) of Compound 6.

$^1$H-NMR ($CDCl_3$): δ 7.63 (1H, d, J=8.0 Hz), 7.31 (1H, d, J=8.0 Hz), 3.21 (2H, t, J=4.8 Hz), 2.82 (2H, t, J=4.8 Hz), 2.53 (2H, t, J=7.2 Hz), 1.83 (2H, t, J=7.2 Hz), 1.78 (4H, m), 1.44 (6H, s).

$^{13}$C-NMR ($CDCl_3$): δ 182.667, 179.142, 162.613, 143.324, 141.832, 134.826, 131.683, 127.983, 121.620, 110.944, 78.949, 31.573, 30.580, 28.774, 26.678, 22.942, 21.911, 15.958.

Example 7

Synthesis of Compound 7

2-Allyloxy-1,4-benzoquinone (10 g, 61 mM) and Styrene (19.8 g, 183 mM) were dissolved in 100 ml of isopropanol and refluxed for 48 hours. The reaction solution was cooled to room temperature, was concentrated by distillation under reduced pressure. 100 ml of toluene added to concentrated solution and toluene was dissolved, and refluxed for 12 hours, and was then purified by chromatography on silica gel to give to 3.4 g (12.9 mM) of 2-Allyl-3-hydroxy-1,4-phenanthrenequinone.

$^1$H-NMR ($CDCl_3$): δ 9.51 (1H, d, J=8.5 Hz), 8.23 (1H, d, J=8.5 Hz), 8.17 (1H, d, J=8.5 Hz), 7.88 (1H, d, J=7.9 Hz), 7.73 (1H, s), 7.72 (1H, m), 7.63 (1H, m), 5.95 (1H, m), 5.20 (1H, d, J=17.1 Hz), 5.07 (1H, d, J=10.0 Hz), 3.37 (2H, d, J=6.5 Hz).

$^{13}$C-NMR ($CDCl_3$): δ 184.917, 183.703, 153.346, 136.428, 135.877, 133.915, 133.804, 130.627, 129.973, 128.935, 128.397, 127.207, 123.927, 122.608, 118.598, 116.261, 27.362.

Mass (m/z): 264(100), 249(13), 236(24), 221(18), 208(19).

The thus-obtained 2-Allyl-3-hydroxy-5,6,7,8-tetrahydro-1,4-phenanthrenequinone and was then mixed with 10 ml of sulfuric acid, without further purification, the resulting mixture was stirred vigorously at room temperature for 10 min and 200 g of ice was added thereto to complete the reaction. 80 ml of $CH_2Cl_2$ was added to the reaction materials which were shaken vigorously. Thereafter, a $CH_2Cl_2$ layer was separated and washed with 5% $NaHCO_3$. An aqueous layer was extracted once again using 30 ml of $CH_2Cl_2$, and combined with the previously extracted organic layer. The organic layer was dried over $MgSO_4$, concentrated to give impure Compound 7. The thus-obtained Compound 7 was first purified by chromatography on silica gel, and then was recrystallized from isopropanol to obtain 2.2 g (8.2 mM) of pure Compound 7.

$^1$H-NMR ($CDCl_3$): δ 9.42 (1H, d, J=8.8 Hz), 8.09 (1H, d, J=8.4 Hz), 7.83 (1H, d, J=8.2 Hz), 7.73 (1H, d, J=8.4 Hz), 7.70 (1H, t, 7.6 Hz), 7.27 (1H, t, J=7.6 Hz), 5.29 (1H, m), 3.29 (1H, dd, J=15.2, 9.8 Hz), 2.75 (1H, dd, J=15.2, 7.3 Hz), 1.61 (3H, d, J=6.3 Hz).

$^{13}$C-NMR ($CDCl_3$): δ 184.064, 175.591, 170.392, 136.064, 135.487, 131.700, 130.730, 128.887, 128.000, 126.853, 125.684, 120.667, 113.494, 84.533, 77.200, 33.437, 22.032.

Mass (m/z): 264(57), 236(100), 218(21), 208(28), 179(32), 165(49).

Example 8

Synthesis of Compound 8

2-Prenyloxy-1,4-benzoquinone (10.0 g, 51.5 mM) and Styrene (60 g, 0.58 M) were dissolved in 120 ml of isopropanol and refluxed for 48 hours. The reaction solution was cooled to room temperature, was concentrated by distillation under reduced pressure, and was then purified by chromatography on silica gel to give to 4.2 g (8.2 mM) of 2-((3-Methyl-1-buten)-3-yl)-3-hydroxy-1,4-phenanthrenequinone.

$^1$H-NMR ($CDCl_3$): δ 9.46 (1H, d, J=8.7 Hz), 8.22 (1H, s), 8.15 (2H, s), 7.88 (1H, d, J=8.1 Hz), 7.73 (1H, m), 7.64 (1H, m), 6.31 (1H, dd, J=17.1 Hz, 10.2 Hz), 5.05 (1H, d, J=17.1 Hz), 4.95 (1H, d, J=10.2 Hz), 1.59 (6H, s).

$^{13}$C-NMR ($CDCl_3$): δ 185.369, 183.928, 152.922, 147.998, 136.533, 135.460, 135.213, 130.584, 129.494, 128.891, 128.312, 127.131, 125.263, 123.011, 122.793, 109.533, 40.615, 28.028.

The thus-obtained 24(3-Methyl-1-buten)-3-yl)-3-hydroxy-1,4-phenanthrenequinone was reacted with sulfuric acid to obtain Compound 8 in the same manner as in Example 7.

$^1$H-NMR ($CDCl_3$): δ 9.42 (1H, d, J=8.8 Hz), 8.10 (1H, d, J=8.4 Hz), 7.84 (1H, d, J=8.1 Hz), 7.76 (1H, d, J=8.4 Hz), 7.69 (1H, t, J=8.2 Hz), 7.56 (1H, t, J=8.2 Hz), 4.71 (1H, q, J=6.6 Hz), 1.50 (3H, d, J=6.6 Hz), 1.47 (3H, s), 1.29 (3H, s).

$^{13}$C-NMR ($CDCl_3$): δ 184.373, 175.649, 168.788, 135.954, 135.254, 131.622, 130.594, 129.096, 128.849, 127.898, 126.809, 125.806, 121.768, 120.625, 92.860, 44.078, 25.783, 20.481, 14.581.

Example 9

Synthesis of Compound 9

2-Allyloxy-1,4-benzoquinone (10.0 g, 61 mM) and α-Methylstyrene (70 g, 0.59 M) were dissolved in 120 ml of isopropanol to give 3.6 g (14 mM) of 2-Allyl-3-hydroxy-9-methyl-1,4-phenanthrenequinone in the same manner as in Example 7.

$^1$H-NMR ($CDCl_3$): δ 9.55 (1H, dd, J=8.8, 0.8 Hz), 8.06 (1H, s), 8.05 (1H, dd, J=6.7, 1.1 Hz), 7.75 (1H, s), 7.72 (1H, m), 7.63 (1H, m), 5.95 (1H, m), 5.18 (1H, dq, J=17.1, 1.6 Hz), 5.06 (1H, dq, J=10.0, 1.6 Hz), 3.35 (2H, dt, J=6.5, 1.6 Hz), 2.79 (3H, s).

$^{13}$C-NMR ($CDCl_3$): δ 184.941, 183.038, 153.243, 144.316, 134.626, 133.982, 133.052, 129.972, 128.063, 127.627, 124.541, 123.446, 122.107, 117.960, 116.156, 27.312, 20.595.

The thus-obtained 2-Allyl-3-hydroxy-9-methyl-1,4-phenanthrenequinone was reacted with sulfuric acid to obtain Compound 9 in the same manner as in Example 7.

$^1$H-NMR ($CDCl_3$): δ 9.47 (1H, d, J=8.7 Hz), 8.00 (1H, d, J=8.5 Hz), 7.69 (1H, m), 7.59 (1H, m), 7.57 (1H, s), 5.26 (1H, m), 3.27 (1H, dd, J=15.2, 9.8 Hz), 2.76 (3H, s), 2.74 (1H, dd, J=15.2, 7.3 Hz), 1.61 (3H, d, J=6.3 Hz).

¹³C-NMR (CDCl₃): δ 183.629, 175.716, 170.346, 144.050, 134.325, 131.821, 130.165, 128.465, 127.748, 127.429, 124.596, 124.080, 121.742, 113.465, 84.429, 33.426, 22.039, 20.537.

Example 10

Synthesis of Compound 10

2-Prenyloxy-1,4-benzoquinone (7.68 g, 40.0 mM) and α-Methylstyrene (48 g, 0.40 M) were dissolved in 100 ml of isopropanol to give 1.74 g (5.7 mM) of 2-((3-Methyl-1-buten)-3-yl)-3-hydroxy-9-methyl-1,4-phenanthrenequinone in the same manner as in Example 7.

¹H-NMR (CDCl₃): δ 9.43 (1H, d, J=8.3 Hz), 8.25 (1H, s), 7.98 (1H, d, J=8.2 Hz), 7.94 (1H, s), 7.66 (1H, t, J=8.3 Hz), 7.59 (1H, J=8.3 Hz), 6.31 (1H, dd, J=17.1 Hz, 10.2 Hz), 5.04 (1H, d, J=17.1 Hz), 4.98 (1H, d, J=10.2 Hz), 2.73 (3H, s), 1.59 (6H, s).

¹³C-NMR (CDCl₃): δ 184.598, 183.422, 152.950, 148.061, 144.555, 134.693, 134.438, 130.021, 129.674, 128.072, 127.662, 124.807, 124.607, 123.781, 121.438, 109.461, 40.558, 28.008, 20.687.

The thus-obtained 24(3-Methyl-1-buten)-3-yl)-3-hydroxy-9-methyl-1,4-phenanthrenequinone was reacted with sulfuric acid to obtain Compound 10 in the same manner as in Example 7.

¹H-NMR (CDCl₃): δ 9.45 (1H, d, J=8.4 Hz), 8.00 (1H, d, J=8.3 Hz), 7.66 (1H, t, J=8.4 Hz), 7.60 (1H, s), 7.57 (1H, t, J=8.4 Hz), 4.69 (1H, q, J=6.7 Hz), 2.76 (3H, s), 1.50 (3H, d, J=6.7 Hz), 1.47 (3H, s), 1.28 (3H, s).

¹³C-NMR (CDCl₃): δ 183.912, 175.781, 168.739, 143.868, 134.065, 131.700, 129.991, 128.609, 127.613, 127.326, 124.508, 124.186, 121.620, 92.711, 44.003, 25.702, 25.282, 20.474, 20.437, 14.521.

Example 11

Synthesis of Compound 11

2-Allyloxy-1,4-benzoquinone (6.56 g, 40 mM) and p-tert-Butylstyrene (70 g, 0.40 M) were dissolved in 80 ml of isopropanol to give 1.90 g (5.9 mM) of 2-Allyl-3-hydroxy-6-tert-butyl-1,4-phenanthrenequinone in the same manner as in Example 7.

¹H-NMR (CDCl₃): δ 9.58 (1H, d, J=0.7 Hz), 8.20 (1H, d, J=8.5 Hz), 8.15 (1H, d, J=8.5 Hz), 7.84 (1H, d, J=8.7 Hz) 7.79 (1H, s), 7.73 (1H, dd, J=8.7, 0.7 Hz), 5.97 (1H, m), 5.17 (1H, d, J=17.1 Hz), 5.06 (1H, d, J=10.0 Hz), 3.37 (2H, d, J=6.4 Hz), 1.47 (9H, s).

¹³C-NMR (CDCl₃): δ 185.133, 183.832, 154.056, 153.423, 135.921, 134.287, 134.001, 133.903, 130.260, 128.539, 127.335, 123.696, 122.307, 122.094, 118.419, 116.164, 35.619, 31.139, 27.374.

Mass (m/z): 320(100), 305(57), 292(7), 277(23), 264(36).

The thus-obtained 2-Allyl-3-hydroxy-6-tert-butyl-1,4-phenanthrenequinone was reacted with sulfuric acid to obtain Compound 11 in the same manner as in Example 7.

¹H-NMR (CDCl₃): δ 9.49 (1H, d, J=0.2 Hz), 8.05 (1H, d, J=8.3 Hz), 7.79 (1H, d, J=8.7 Hz), 7.69 (1H, d, J=8.3 Hz), 7.67 (1H, dd, J=8.7, 0.2 Hz), 5.29 (1H, m), 3.29 (1H, dd, J=15.2, 9.8 Hz), 2.75 (1H, dd, J=15.2, 7.3 Hz), 1.61 (3H, d, J=6.3 Hz), 1.44 (9H, s).

¹³C-NMR (CDCl₃): δ 184.387, 175.790, 170.697, 154.084, 135.449, 133.959, 131.978, 128.829, 128.456, 127.016, 125.518, 121.988, 120.074, 113.284, 84.471, 35.632, 33.432, 31.033, 22.023.

Mass (m/z): 320(36), 292(100), 277(74), 266(13), 249(13), 236(43).

Example 12

Synthesis of Compound 12

2-Prenyloxy-1,4-benzoquinone (7.68 g, 40 mM) and p-tert-Butylstyrene (70 g, 0.40M) were dissolved in 80 ml of isopropanol to give 1.7 g (4.9 mM) of 2-((3-Methyl-1-buten)-3-yl)-3-hydroxy-6-tert-butyl-1,4-phenanthrenequinone in the same manner as in Example 7.

¹H-NMR (CDCl₃): δ 9.52 (1H, d, J=1.8 Hz), 8.27 (1H, s), 8.13 (2H, s), 7.83 (1H, d, J=8.6 Hz), 7.72 (1H, dd, J=8.6, 1.8 Hz), 6.31 (1H, dd, J=17.4 Hz, 10.6 Hz), 5.03 (1H, d, J=17.4 Hz), 4.98 (1H, d, J=10.6 Hz), 1.59 (6H, s), 1.47 (9H, s).

¹³C-NMR (CDCl₃): δ 184.594, 184.024, 153.989, 152.986, 148.093, 136.032, 135.320, 133.855, 129.782, 128.494, 127.545, 127.214, 125.127, 122.821, 122.271, 109.449, 40.598, 35.581, 31.146, 28.053.

The thus-obtained 2-((3-Methyl-1-buten)-3-yl)-3-hydroxy-6-tert-butyl-1,4-phenanthrenequinone was reacted with sulfuric acid to obtain compound 12 in the same manner as in Example 7.

¹H-NMR (CDCl₃): δ 9.47 (1H, d, J=0.9 Hz), 8.05 (1H, d, J=8.3 Hz), 7.78 (1H, d, J=8.7 Hz), 7.70 (1H, d, J=8.3 Hz), 7.66 (1H, dd, J=8.7, 1.8 Hz), 4.70 (1H, q, J=6.7 Hz), 1.49 (3H, d, J=6.7 Hz), 1.47 (3H, s), 1.43 (9H, s), 1.29 (3H, s).

¹³C-NMR (CDCl₃): δ 184.614, 175.778, 168.984, 153.912, 135.320, 133.718, 131.921, 129.043, 128.398, 126.854, 125.688, 122.015, 121.580, 120.002, 92.747, 44.070, 35.591, 31.069, 25.792, 20.478, 14.543.

Example 13

Synthesis of Compound 13

2-Allyloxy-1,4-benzoquinone (6.56 g, 40 mM) and p-Chlorostyrene (60 g, 0.44 M) were dissolved in 80 ml of isopropanol to give 0.74 g (2.48 mM) of 2-Allyl-3-hydroxy-6-chloro-1,4-phenanthrenequinone in the same manner as in Example 7.

¹H-NMR (CDCl₃): δ 9.62 (1H, d, J=1.2 Hz), 8.23 (1H, d, J=8.5 Hz), 8.19 (1H, d, J=8.5 Hz), 7.83 (1H, d, J=8.7 Hz) 7.69 (1H, s), 7.67 (1H, dd, J=8.7, 1.2 Hz), 5.93 (1H, m), 5.21 (1H, d, J=17.1 Hz), 5.04 (1H, d, J=10.0 Hz), 3.39 (2H, d, J=6.4 Hz).

¹³C-NMR (CDCl₃): δ 184.518, 183.272, 153.335, 150.643, 137.202, 136.188, 134.327, 134.063, 133.746, 130.418, 130.234, 129.423, 126.278, 122.953, 118.952, 116.424, 27.392.

The thus-obtained 2-Allyl-3-hydroxy-6-chloro-1,4-phenanthrenequinone was reacted with sulfuric acid to obtain Compound 13 in the same manner as in Example 7.

¹H-NMR (CDCl₃): δ 9.37 (1H, d, 1.8 Hz), 8.03 (1H, d, J=8.6 Hz), 7.72 (1H, d, J=5.2 Hz), 7.69 (1H, d, J=5.2 Hz), 7.45 (1H, dd, J=8.6, 1.8 Hz), 5.30 (1H, m), 3.27 (1H, dd, J=15.2, 9.8 Hz), 2.74 (1H, dd, J=15.2, 7.3 Hz), 1.62 (3H, d, J=6.3 Hz).

¹³C-NMR (CDCl₃): δ 183.222, 175.000, 169.731, 137.263, 135.873, 133.498, 131.861, 130.886, 130.196, 129.673, 128.889, 128.769, 125.700, 114.025, 84.640, 33.425, 21.994.

Example 14

Synthesis of Compound 14

2-Allyloxy-1,4-benzoquinone (6.56 g, 40 mM) and p-Methylstyrene (17.4 g, 0.10 M) were dissolved in 80 ml of isopropanol to give 2.3 g (8.3 mM) of 2-Allyl-3-hydroxy-6-methyl-1,4-phenanthrenequinone in the same manner as in Example 7.

$^1$H-NMR (CDCl$_3$): δ 9.58 (1H, s), 8.19 (1H, d, J=8.5 Hz), 8.16 (1H, d, J=8.5 Hz), 7.80 (1H, d, J=8.7 Hz) 7.77 (1H, s), 7.47 (1H, d, J=8.7 Hz), 5.97 (1H, m), 5.21 (1H, d, J=17.1 Hz), 5.06 (1H, d, J=10.0 Hz), 3.39 (2H, d, J=6.4 Hz), 2.62 (3H, s).

The thus-obtained 2-Allyl-3-hydroxy-6-methyl-1,4-phenanthrenequinone was reacted with sulfuric acid to obtain Compound 14 in the same manner as in Example 7.

$^1$H-NMR (CDCl$_3$): δ 9.20 (1H, d, J=1.2 Hz), 8.01 (1H, d, J=8.3 Hz), 7.71 (1H, d, J=8.4 Hz), 7.64 (1H, d, J=8.3 Hz), 7.38 (1H, dd, J=8.4, 1.2 Hz), 5.27 (1H, m), 3.27 (1H, dd, J=15.1, 9.8 Hz), 2.74 (1H, dd, J=15.2, 7.3 Hz), 2.56 (3H, s), 1.60 (3H, d, J=6.3 Hz).

$^{13}$C-NMR (CDCl$_3$): δ 184.077, 175.675, 170.463, 141.211, 135.671, 133.912, 131.946, 130.192, 128.817, 128.635, 125.669, 124.943, 119.782, 113.318, 84.393, 33.411, 22.486, 21.992.

Example 15

Synthesis of Compound 15

2-Allyloxy-1,4-benzoquinone (6.56 g, 40 mM) and p-Methoxystyrene (59 g, 0.44 M) were dissolved in 80 ml of isopropanol to give 1.1 g (3.4 mM) of 2-Allyl-3-hydroxy-6-methyl-1,4-phenanthrenequinone in the same manner as in Example 7.

$^1$H-NMR (CDCl$_3$): δ 9.32 (1H, d, J=1.4 Hz), 8.17 (1H, d, J=8.5 Hz), 8.12 (1H, d, J=8.5 Hz), 7.77 (1H, d, J=8.4 Hz), 7.73 (1H, s), 7.45 (1H, dd, J=8.4, 1.4 Hz) 5.93 (1H, m), 5.19 (1H, dd, J=17.1, 1.5 Hz), 5.07 (1H, d, J=13.2, 1.5 Hz), 3.36 (2H, dt, J=6.5, 1.4 Hz), 2.60 (3H, s).

$^{13}$C-NMR (CDCl$_3$): δ 184.992, 183.581, 153.318, 141.214, 136.154, 134.237, 133.983, 133.847, 130.572, 130.251, 128.701, 126.073, 123.125, 121.778, 118.377, 116.214, 27.389, 22.527.

The thus-obtained 2-Allyl-3-hydroxy-6-methoxy-1,4-phenanthrenequinone was reacted with sulfuric acid to obtain Compound 15 in the same manner as in Example 7.

$^1$H-NMR (CDCl$_3$): δ 8.93 (1H, d, J=2.4 Hz), 8.01 (1H, d, J=8.2 Hz), 7.71 (1H, d, J=9.0 Hz), 7.59 (1H, d, J=8.2 Hz), 7.20 (1H, dd, J=9.0, 2.4 Hz) 5.28 (1H, m), 3.99 (3H, s), 3.29 (1H, dd, J=15.2, 9.8 Hz), 2.75 (2H, dd, J=15.2, 7.3 Hz), 1.61 (3H, d, J=6.3 Hz).

$^{13}$C-NMR (CDCl$_3$): δ 183.888, 175.545, 170.548, 161.891, 135.711, 133.753, 131.541, 130.368, 129.203, 123.512, 121.403, 118.612, 113.467, 104.104, 84.385, 55.493, 33.403, 22.007.

Example 16

Synthesis of Compound 16

2-Methoxy-1,4-benzoquinone (30.0 g, 72 mM) and α-Methylstyrene (236 g, 2.0 M) were dissolved in 290 ml of isopropanol and refluxed for 30 hours. The reaction solution was subjected to vacuum distillation to recover isopropanol and α-Methylstyrene, and the reaction solution was concentrated. The resulting product was purified by chromatography to give to 1.38 g (5.47 mM) of 3-Methoxy-9-methyl-1,4-phenanthrenequinone.

$^1$H-NMR (CDCl$_3$): δ 9.57 (1H, d, J=8.5 Hz), 8.07 (1H, J=8.5 Hz), 8.03 (1H, s), 7.73 (1H, t, J=8.5 Hz), 7.65 (1H, t, J=8.5 Hz), 6.12 (1H, s), 3.96 (3H, s), 2.81 (3H, s).

3-Methoxy-9-methyl-1,4-phenanthrenequinone (1.17 g, 4.63 mM) was dissolved in 40 ml of methanol solution containing 5% NaOH, and the resulting solution was vigorously stirred at room temperature for 1 hour. The reaction solution was neutralized by 1N HCl and was then concentrated by distillation under reduced pressure. The resulting purified by chromatography to give 0.34 g (1.42 mM) of 3-Hydroxy-9-methyl-1,4-phenanthrenequinone.

$^1$H-NMR (CDCl$_3$): δ 9.61 (1H, d, J=8.5 Hz), 8.10 (1H, s), 8.07 (1H, d, J=8.5 Hz), 7.78 (1H, t, J=8.5 Hz), 7.69 (1H, t, J=8.5 Hz), 6.32 (1H, s), 2.82 (3H, s).

3-Hydroxy-9-methyl-1,4-phenanthrenequinone (0.34 g, 1.42 mM) was dissolved in 10 ml of DMSO, and was cooled −50° C., and then 20 mg of LiH was gradually added thereto. The reaction solution was vigorously stirred at room temperature, and after confirming no further production of hydrogen, was additionally stirred for another 30 min.

Prenyl bromide (1-Bromo-3-methyl-2-butene) (220 mg, 1.48 mM) and LiI (40 mg) were gradually added thereto. The reaction solution was heated to 45° C. and then stirred vigorously for 12 hours at that temperature. The reaction solution was cooled below 10° C., and 5 ml of cold water was first added. Thereafter, 1N HCl was gradually added to maintain the resulting solution at an acidic pH>3. 20 ml of CH$_2$Cl$_2$ was added to the reaction mixture which was then vigorously shaken to separate organic layers. The organic layer was washed with 10 ml of 5% NaHCO$_3$, and was concentrated. The resulting concentrates were purified by chromatography on silica gel to give 116 mg (0.38 mM) of 2-Prenyl-3-hydroxy-9-methyl-1,4-phenanthrenequinone.

$^1$H-NMR (CDCl$_3$): δ 9.60 (1H, d, J=8.5 Hz), 8.13 (1H, s), 8.08 (1H, d, J=8.5 Hz), 7.72 (1H, t, J=8.5 Hz), 7.62 (1H, t, J=8.5 Hz), 5.26 (1H, m), 3.34 (1H, d, J=7.1 Hz), 2.83 (3H, s), 1.82 (3H, s), 1.71 (3H, s).

2-Prenyl-3-hydroxy-9-methyl-1,4-phenanthrenequinone (116 mg, 0.38 mM) was mixed with 2 ml of sulfur acid, and was vigorously stirred at room temperature for 10 min and 10 g of ice was added thereto to complete the reaction. 20 ml of CH$_2$Cl$_2$ was added to the reaction materials which were then shaken vigorously. Thereafter, a CH$_2$Cl$_2$ layer was separated and washed with 5% NaHCO$_3$. An aqueous layer was extracted once again using 10 ml of CH$_2$Cl$_2$, washed with 5% NaHCO$_3$ and combined with the previously extracted organic layer. The organic layer was concentrated over MgSO$_4$ and concentrates were purified by chromatography on silica gel to give 0.83 g (2.7 mM) of Compound 16

$^1$H-NMR (CDCl$_3$): δ 9.45 (1H, d, J=7.0 Hz), 7.99 (1H, d, 6.8 Hz), 7.79 (1H, s), 7.67 (1H, t, J=7.0 Hz), 7.57 (1H, t, J=7.0 Hz), 2.78 (3H, s), 2.55 (2H, t, J=4.5 Hz), 1.86 (2H, t, J=4.5 Hz), 1.50 (6H, s).

$^{13}$C-NMR (CDCl$_3$): δ 182.593, 179.564, 162.322, 144.079, 134.093, 133.772, 131.808, 130.204, 127.888, 127.642, 124.614, 123.953, 121.846, 111.762, 79.699, 31.861, 27.035, 20.972, 16.288.

Experimental Example 1

Determination of AMPK Activation

Myoblast cells, C2C12, were cultured in DMEM containing 10% bovine calf serum. When a cell density reached a range of about 85% to 90%, the culture medium was replaced with a medium containing 1% bovine calf serum to induce differentiation of cells. The thus-differentiated myoblast cells were treated with samples synthesized in Examples 1 through 16 at a concentration of 5 μg/ml, and compared with a control group. Enzymatic activity of AMPK was determined as follows. Firstly, C2C12 cells were lysed to obtain protein extracts and then ammonium sulfate was added to a final concentration of 30%, thereby precipitating proteins. Protein precipitates were dissolved in a buffer (62.5 mM Hepes, pH 7.2, 62.5 mM NaCl, 62.5 mM NaF, 1.25 mM Na pyrophosphate, 1.25 mM EDTA, 1 mM DTT, 0.1 mM PMSF, and 200 μM AMP). Thereafter, 200 μM SAMS peptide (HMRSAM SGLHLVKRR: the underlined serine residue is a phosphorylation site, as an AMPK phosphorylation site of acetyl-CoA carboxylase) and [γ-32P]ATP were added thereto and reactants were reacted for 10 minutes at 30° C. This was followed by spotting of the resulting reaction solution on p81 phosphocellulose paper. The p81 paper was washed with a 3% phosphoric acid solution and radioactivity thereof was measured. For each reaction condition, reactions involving no SAMS peptide were also conducted and basic values were subtracted from the thus-observed values.

The results thus obtained are shown in Table 2.

TABLE 2

| Compound | AMPK fold |
|---|---|
| DMSO (0.5%) | 1 |
| Example 1 | 2.2 |
| Example 2 | 2.4 |
| Example 3 | 2.2 |
| Example 4 | 2.2 |
| Example 5 | 2.3 |
| Example 6 | 2.2 |
| Example 7 | 2.2 |
| Example 8 | 2.5 |
| Example 9 | 2.3 |
| Example 10 | 2.4 |
| Example 11 | 2.3 |
| Example 12 | 2.2 |
| Example 13 | 2.3 |
| Example 14 | 2.5 |
| Example 15 | 2.2 |
| Example 16 | 1.9 |

As can be seen from Table 2, when compounds according to Examples of the present invention were treated on myoblast cells, C2C12, this treatment leads to increased enzymatic activity of AMPK.

Experimental Example 2

Weight Loss Effects in Obese Mice (ob/ob)

10-week-old C57BL/6JL Lep ob/Lep ob male mice having obesity characteristics and predisposition were purchased from Daehan Biolink Co., Ltd. (Chungchongbuk-do, Korea). Animals were raised in a breeding room maintained at a temperature of 23° C., 55% humidity, illumination of 300 to 500 lux, a 12-h light/dark (L/D) cycle, and ventilation of 10 to 18 times/hr. Animals were fed ad libitum pellets of Purina Rodent Laboratory Chow 5001 (purchased from Purina Mills Inc., St. Louis, Mo., USA) as a solid feed for experimental animals and tap water as drinking water. Mice were allowed to acclimate to new environment of the breeding room for two weeks and were then administered some pyrano-3,4-phenanthrenequinone or furano-3,4-naphthoquinone derivatives synthesized according to the present invention at mixed-feed of 0.4% for 18 days. Observation was made on changes in body weight, blood glucose and dietary intake, with respect to a time course of administration. After administration was complete, confirm changes in glucose, lipid and enzyme levels in blood.

For comparison, the same experiments were carried out for the subject (negative control group) to which the active ingredient was not administered, and subject (positive control group) to which Cryptotanshinone, extracted from Danshen by a method as set forth in Example 1 of the Korean Patent Application No. 2004-0116339 by the present applicant, was administered by the above-mentioned condition.

Table 3 below shows results of changes over time in body weight of C57BL/6JL Lep ob/Lep ob mice. Herein, 'Increase in BW' is calculated as the following;

Increase in BW=(Final BW−Initial BW)/Initial BW×100

TABLE 3

| Sample | Initial BW (g) | Final BW (g) | Increase in BW (%) |
|---|---|---|---|
| Negative control group | 53.2 ± 1.2 | 55.5 ± 0.9 | 4.3 |
| Positive control group | 52.2 ± 1.7 | 51.6 ± 1.7 | −1.2 |
| Example 1 | 52.8 ± 2.2 | 45.3 ± 1.7 | −14.2 |
| Example 2 | 52.8 ± 2.8 | 44.4 ± 3.4 | −15.9 |
| Example 3 | 52.3 ± 1.8 | 46.1 ± 2.1 | −11.9 |
| Example 4 | 52.3 ± 2.3 | 48.6 ± 3.3 | −7.1 |
| Example 5 | 52.0 ± 1.6 | 47.9 ± 3.1 | −7.8 |
| Example 6 | 52.3 ± 1.6 | 49.0 ± 2.7 | −6.3 |
| Example 7 | 51.6 ± 1.8 | 49.6 ± 2.6 | −3.9 |
| Example 8 | 51.6 ± 2.0 | 41.1 ± 1.3 | −20.3 |
| Example 9 | 52.0 ± 0.8 | 48.9 ± 1.7 | −6.0 |
| Example 10 | 51.6 ± 2.0 | 41.1 ± 1.3 | −20.3 |
| Example 11 | 52.9 ± 1.2 | 52.2 ± 1.4 | −1.2 |
| Example 12 | 51.9 ± 2.1 | 48.3 ± 2.3 | −6.9 |
| Example 13 | 52.1 ± 2.7 | 48.8 ± 2.5 | −6.3 |
| Example 14 | 52.4 ± 2.3 | 48.7 ± 1.9 | −7.0 |
| Example 15 | 52.0 ± 1.9 | 48.5 ± 1.5 | −6.7 |
| Example 16 | 51.7 ± 1.6 | 48.0 ± 1.9 | −7.2 |

As can be seen from Table 3 above, administration of the compounds according to the Examples of present invention leads to a significant reduction in body weight, as compared to the negative control group and, in most of case, leads to a significant reduction in body weight, as compared to the positive control group.

Figure 2:
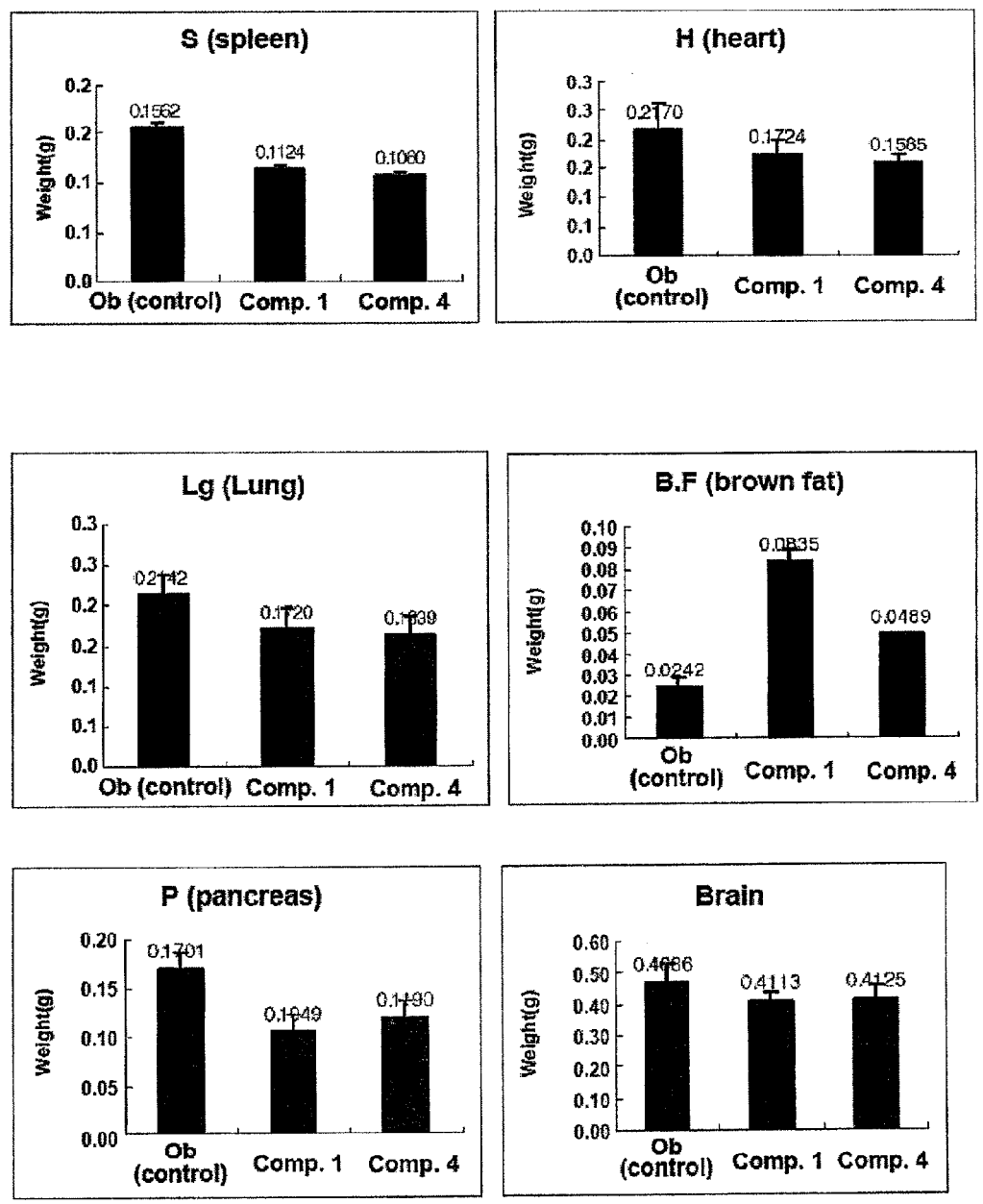
Figure 3:
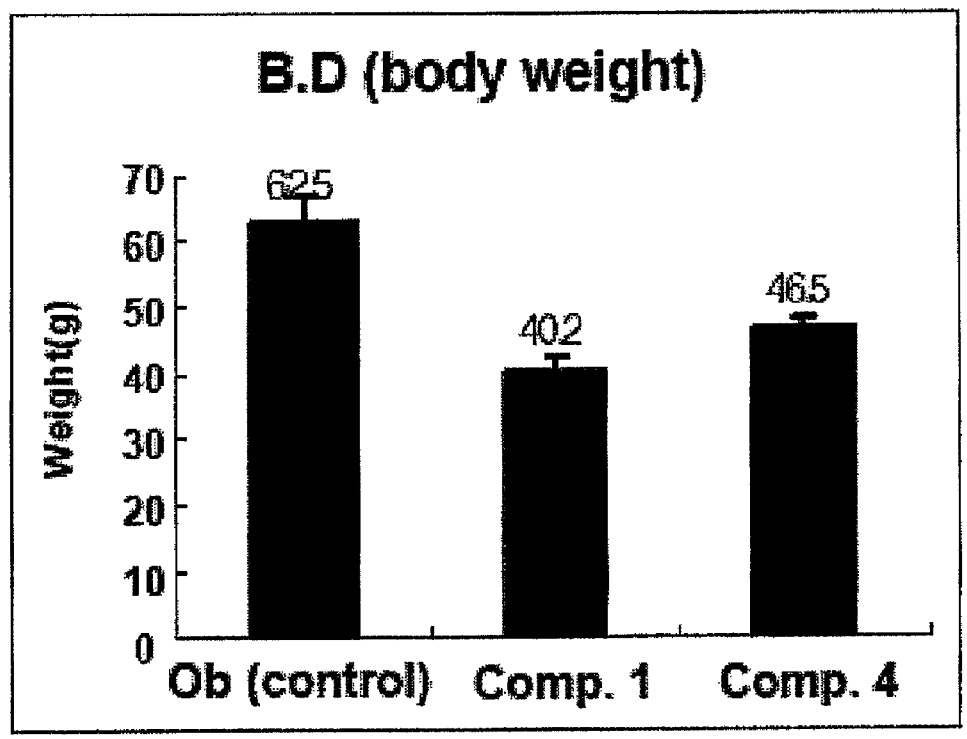

FIGS. 1 through 3 disclose fat distribution in terms of numerical values for the respective organs of C57BL/6JL Lep ob/Lep ob mice to which compounds as set forth in Table 3 were administered. As can be seen from graphs given in FIGS. 1 through 3, the experimental groups to which the compounds according to the present invention were administered exhibited a significant reduction in fat content of tissues for all organs, and further exhibited increases in brown fat (see, FIG. 2) contents compared with the control group, indicating that fat metabolism was significantly increased.

Table 4 below shows changes in blood biomarker which is lipid and glucose levels of C57BL/6JL Lep ob/Lep ob mice to which the Examples of the present invention were administered.

TABLE 4

| Sample | GOT | GPT | glucose | T. chol | HDL chol | LDL chol | triglyceride |
|---|---|---|---|---|---|---|---|
| Negative Con. | 735.0 | 441.7 | 228 | 178.3 | 51.7 | 15.00 | 95.0 |
| Positive Con. | 255.0 | 149.0 | — | 135.0 | 48.0 | 11.0 | 100.9 |
| Ex. 1 | 233.3 | 118.8 | 120 | 141.7 | 42.5 | 13.00 | 81.7 |
| Ex. 2 | 378.8 | 215.0 | 125 | 125.0 | 38.8 | 21.67 | 58.8 |
| Ex. 3 | 247.5 | 160.0 | 132 | 134.0 | 42.5 | 12.00 | 61.7 |
| Ex. 4 | 476.7 | 285.0 | 128 | 127.5 | 45.0 | 10.00 | 76.7 |
| Ex. 5 | 377.5 | 251.0 | 141 | 126.5 | 45.5 | 14.05 | 77.0 |

TABLE 4-continued

| Sample | GOT | GPT | glucose | T. chol | HDL chol | LDL chol | triglyceride |
|---|---|---|---|---|---|---|---|
| Ex. 6 | 392.5 | 250.0 | 145 | 129.5 | 49.0 | 13.00 | 69.5 |
| Ex. 7 | 286.7 | 143.8 | 156 | 148.8 | 58.8 | 14.00 | 70.0 |
| Ex. 8 | 376.5 | 241.0 | 118 | 132.5 | 48.0 | 13.75 | 79.5 |
| Ex. 9 | 355.0 | 77.0 | 136 | 135.0 | 48.0 | 11.00 | 72.0 |
| Ex. 10 | 283.3 | 66.7 | 121 | 115.0 | 45.0 | 5.00 | 88.3 |
| Ex. 11 | 347.5 | 197.5 | 175 | 134.0 | 47.5 | 9.95 | 82.0 |
| Ex. 12 | 355.0 | 77.0 | 153 | 135.0 | 48.0 | 11.00 | 69.0 |
| Ex. 13 | 373.5 | 184.0 | 138 | 125.5 | 44.0 | 12.00 | 85.3 |
| Ex. 14 | 283.3 | 66.7 | 146 | 115.0 | 45.0 | 5.00 | 88.3 |
| Ex. 15 | 312.5 | 206.7 | 155 | 142.0 | 46.0 | 8.75 | 79.0 |
| Ex. 16 | 342.5 | 197.5 | 135 | 140.0 | 47.0 | 12.00 | 82.3 |

As can be seen from Table 4 above, the groups to which the compounds according to Examples of the present invention were administered exhibited a significant reduction in triglyceride, cholesterol and glucose levels in the blood, as compared to the control groups. Particularly, in triglyceride level, compounds according to Examples of the present invention leads to a significant reduction as compared to the positive control group to which the tanshinone derivatives extracted from Danshen were administered, Experimental Example 3

Acute Toxicity Test

1. Oral Administration

Sprague-Dawley rats, weighing 250±7 g (Jung-Ang Lab Animal Inc., Seoul, Korea) were divided into 4 groups, consisting of 10 animals each, and were orally administered Examples 1 to 16 in accordance with the present invention at doses of 100, 250 and 500 mg/kg, respectively. After oral administration, upon observing for 2 weeks whether toxicity was exhibited or not, none of the animals died in all four groups and no visually observable symptoms with exception of weight loss were noticed compared to the control group.

2. Peritoneal Administration

Sprague-Dawley rats, weighing 255±6 g (Jung-Ang Lab Animal Inc., Seoul, Korea) were divided into 4 groups, consisting of 10 animals each, and were peritoneally administered Examples 1 to 16 in accordance with the present invention at doses of 10, 50 and 100 mg/kg, respectively. After peritoneal administration, upon observing for 2 weeks whether toxicity was exhibited or not, none of the animals died in all four groups and no visually observable symptoms with exception of weight loss were noticed compared to the control group.

It was confirmed from the above-mentioned results that the compounds in accordance with the present invention have no acute toxicity.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As apparent from the foregoing, the compounds in accordance with the present invention exhibit excellent effects on increasing the activity of 5' AMP-activated protein kinase (AMPK), thus a pharmaceutical composition using the above-mentioned compounds as an active ingredient exhibit superior effects on the treatment and/or prevention of metabolic syndromes including various disease such as obesity.

What is claimed is:

1. A pharmaceutical composition, comprising:
   (a) a therapeutically effective amount of a compound represented by Formula 1:

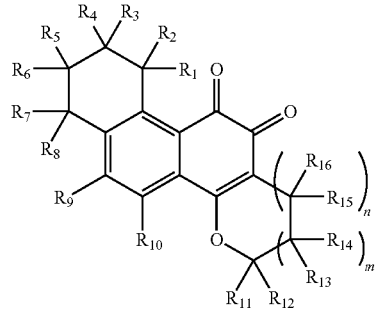

(1)

wherein $R_1$, $R_2$, $R_3$, $R_4$, $R_5$, $R_6$, $R_7$ and $R_8$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl, or heterocycloalkyl, $C_4$-$C_{10}$ aryl or heteroaryl, or two substituents thereof may be taken together to form a cyclic structure or form a double bond;

$R_9$ and $R_{10}$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl, or heterocycloalkyl, $C_4$-$C_{10}$ aryl or heteroaryl;

$R_{11}$, $R_{12}$, $R_{13}$, $R_{14}$, $R_{15}$ and $R_{16}$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl, or heterocycloalkyl, $C_4$-$C_{10}$ aryl or heteroaryl, or two substituents thereof may be taken together to form a cyclic structure or form a double bond;

m and n are each independently 0 or 1, when m or n is 0, carbon atoms adjacent to m or n may form a cyclic structure via a direct bond;

with the proviso that (i) when m is 1, n is 0, carbon atoms adjacent to m or n form a cyclic structure via a direct bond, $R_9$, $R_{10}$ and $R_{11}$ are hydrogen, $R_{12}$ and $R_{13}$ are hydrogen or are taken together to form a double bond, and $R_1$ to $R_6$ are hydrogen and $R_7$ and $R_8$ are methyl, $R_{14}$ is not methyl, and (ii) when m is 1, n is 0, carbon atoms adjacent to m or n form a cyclic structure via a direct bond, $R_9$, $R_{10}$ and $R_{11}$ are hydrogen, $R_{12}$ and $R_{13}$ are hydrogen or are taken together to form a double bond, $R_1$, $R_3$ and $R_5$ are hydrogen, $R_2$, $R_4$, $R_6$ and $R_8$ are taken together to form a double bond, and $R_7$ is methyl, $R_{14}$ is not methyl; and (b) a pharmaceutically acceptable carrier, a diluent, an excipient, or any combination thereof.

2. The pharmaceutical composition according to claim 1, wherein the compound of Formula 1 is selected from compounds of Formulae 2 and 3:

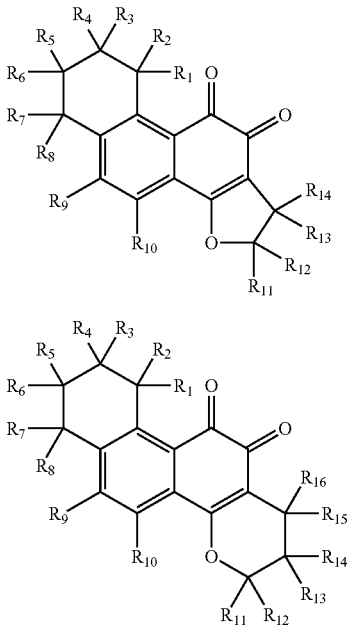

(2)

(3)

wherein, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are as defined in Formula 1.

3. The pharmaceutical composition according to claim 1, wherein the compound of Formula 1 is selected from compounds of Formulae 4 and 5:

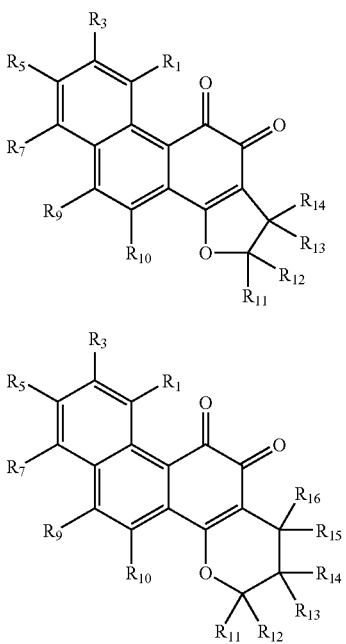

(4)

(5)

wherein, $R_1$, $R_3$, $R_5$, $R_7$, $R_9$, $R_{10}$, $R_{11}$, $R_{12}$, $R_{13}$, $R_{14}$ $R_{15}$, and $R_{16}$ are as defined in Formula 1.

4. The pharmaceutical composition according to claim 1, wherein the compound of Formula 1 is a compound wherein $R_1$, $R_2$, $R_3$, $R_4$, $R_5$, $R_6$, $R_7$ and $R_8$ are each independently selected from the group consisting hydrogen, halogen, $C_1$-$C_6$ alkyl and $C_1$-$C_6$ alkyloxy, or two substituents thereof are taken together to form a double bond, and $R_9$, $R_{10}$ $R_{11}$, $R_{12}$, $R_{13}$, $R_{14}$, $R_{15}$ and $R_{16}$ are each independently hydrogen or $C_1$-$C_6$ alkyl.

5. The pharmaceutical composition according to claim 1, wherein the compound of Formula 1 is any one of compounds below:

2-Methyl-1,2,6,7,8,9-hexahydro-phenanthro[1,2-b]furan-10,11-dione 2,6,6-Trimethyl-1,2,6,7,8,9-hexahydro-phenanthro[1,2-b]furan-10,11-dione 2,6,6-Trimethyl-1,2,6,7,8,9-hexahydro-phenanthro[1,2-b]furan-10,11-dione 1,1,2,6,6-Pentamethyl-1,2,6,7,8,9-hexahydro-phenanthro[1,2-b]furan-10,11-dione 1,2,2,6,6-Pentamethyl-1,2,6,7,8,9-hexahydro-phenanthro[1,2-b]furan-10,11-dione 3,3-Dimethyl-2,3,7,8,9,10-hexahydro-1H-4-oxa-chrysene-11,12-dione 2-Methyl-1,2-dihydro-phenanthro[1,2-b]furan-10,11-dione 1,1,2-Trimethyl-1,2-dihydro-phenanthro[1,2-b]furan-10,11-dione 2,5-Dimethyl-1,2-dihydro-phenanthro[1,2-b]furan-10,11-dione 1,1,2,5-Tetramethyl-1,2-dihydro-phenanthro[1,2-b]furan-10,11-dione 8-tert-Butyl-2-methyl-1,2-dihydro-phenanthro[1,2-b]furan-10,11-dione 8-tert-Butyl-1,1,2-trimethyl-1,2-dihydro-phenanthro[1,2-b]furan-10,11-dione 8-Chloro-2-methyl-1,2-dihydro-phenanthro[1,2-b]furan-10,11-dione 2,8-Dimethyl-1,2-dihydro-phenanthro[1,2-b]furan-10,11-dione 8-Methoxy-2-methyl-1,2-dihydro-phenanthro[1,2-b]furan-10,11-dione 3,3,6-Trimethyl-2,3-dihydro-1H-4-oxa-chrysene-11,12-dione.

6. A compound represented by the following Formula 1-1:

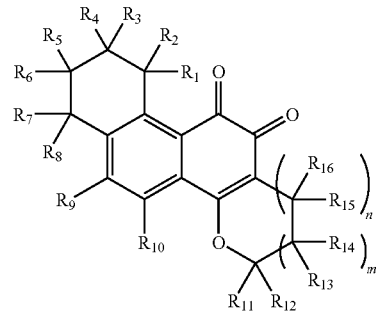

(1-1)

wherein $R_1$, $R_2$, $R_3$, $R_4$, $R_5$, $R_6$, $R_7$ and $R_8$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl, or heterocycloalkyl, $C_4$-$C_{10}$ aryl or heteroaryl, or two substituents thereof may be taken together to form a cyclic structure or form a double bond;

$R_9$ and $R_{10}$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl, or heterocycloalkyl, $C_4$-$C_{10}$ aryl or heteroaryl;

$R_{11}$, $R_{12}$, $R_{13}$, $R_{14}$, $R_{15}$ and $R_{16}$ are each independently hydrogen, halogen, hydroxyl, $C_1$-$C_6$ alkyl, $C_1$-$C_6$ alkene, $C_1$-$C_6$ alkyloxy, $C_3$-$C_8$ cycloalkyl or heterocycloalkyl, $C_4$-$C_{10}$ aryl or heteroaryl, or two substituents thereof may be taken together to form a cyclic structure or form a double bond;

m and n are each independently 0 or 1, when m or n is 0, carbon atoms adjacent to m or n may form a cyclic structure via a direct bond; and with the proviso that (i) when m is 1, n is 0, carbon atoms adjacent to m or n form a cyclic structure via a direct bond, $R_9$ and $R_{10}$ are hydrogen, $R_1$ to $R_6$ are hydrogen, and $R_7$ and $R_8$ are methyl, if $R_{12}$ and $R_{13}$ is hydrogen, then $R_{11}$ or $R_{14}$ is not methyl, (ii) when m is 1, n is 0, carbon atoms adjacent to m or n form a cyclic structure via a direct bond, $R_9$, and $R_{10}$ are hydrogen, $R_1$ to $R_6$ are hydrogen and $R_7$ and $R_8$ are methyl, if $R_{12}$ and $R_{13}$ form a double bond, then $R_{14}$ is not methyl, iii) when m is 1, n is 0, carbon atoms adjacent to m or n form a cyclic structure via a direct bond, $R_9$, and $R_{10}$ are hydrogen, $R_1$, $R_3$ and $R_5$ are hydrogen, $R_2$, $R_4$, $R_6$ and $R_8$ are taken together to form a double bond, if $R_7$ is methyl and $R_{12}$ and $R_{13}$ are hydrogen, then $R_{14}$ is not methyl, (iv) when m is 1, n is 0, carbon atoms adjacent to m or n form a cyclic structure via a direct bond, $R_9$, and $R_{10}$ are hydrogen $R_1$, $R_3$ and $R_5$ are hydrogen, $R_2$, $R_4$, $R_6$ and $R_8$ are taken together to form a double bond, if $R_7$ is hydrogen and $R_{12}$ and $R_{13}$ are hydrogen, then $R_{11}$ is not methyl, (v) when m is 1, n is 0, carbon atoms adjacent to m or n form a cyclic structure via a direct bond, $R_9$, and $R_{10}$ are hydrogen, $R_1$, $R_3$ and $R_5$ are hydrogen, $R_2$, $R_4$, $R_6$ and $R_8$ are taken together to form a double bond, and if $R_7$ is methyl and $R_{12}$ and $R_{13}$ form a double bond, then $R_{14}$ is not methyl.

7. The compound or an isomer, prodrug, or solvate thereof according to claim 6, wherein the compound of Formula 1-1 is a compound wherein $R_1$, $R_2$, $R_3$, $R_4$, $R_5$, $R_6$, $R_7$ and $R_8$ are each independently selected from the group consisting hydrogen, halogen, $C_1$-$C_6$ alkyl and $C_1$-$C_6$ alkyloxy, or two substituents thereof are taken together to form a double bond, and $R_9$, $R_{10}$, $R_{11}$, $R_{12}$, $R_{13}$, $R_{14}$, $R_{15}$ and $R_{16}$ are each independently hydrogen or $C_1$-$C_6$ alkyl.

8. The compound according to claim 6, wherein the compound of Formula 1-1 is any one of compounds below:
2-Methyl-1,2,6,7,8,9-hexahydro-phenanthro[1,2-b]furan-10,11-dione
2,6,6-Trimethyl-1,2,6,7,8,9-hexahydro-phenanthro[1,2-b]furan-10,11-dione
1,1,2,6,6-Pentamethyl-1,2,6,7,8,9-hexahydro-phenanthro[1,2-b]furan-10,11-dione
1,2,2,6,6-Pentamethyl-1,2,6,7,8,9-hexahydro-phenanthro[1,2-b]furan-10,11-dione
3,3-Dimethyl-2,3,7,8,9,10-hexahydro-1H-4-oxa-chrysene-11,12-dione
1,1,2-Trimethyl-1,2-dihydro-phenanthro[1,2-b]furan-10,11-dione
2,5-Dimethyl-1,2-dihydro-phenanthro[1,2-b]furan-10,11-dione
1,1,2,5-Tetramethyl-1,2-dihydro-phenanthro[1,2-b]furan-10,11-dione
8-tert-Butyl-2-methyl-1,2-dihydro-phenanthro[1,2-b]furan-10,11-dione
8-tert-Butyl-1,1,2-trimethyl-1,2-dihydro-phenanthro[1,2-b]furan-10,11-dione
8-Chloro-2-methyl-1,2-dihydro-phenanthro[1,2-b]furan-10,11-dione
2,8-Dimethyl-1,2-dihydro-phenanthro[1,2-b]furan-10,11-dione
8-Methoxy-2-methyl-1,2-dihydro-phenanthro[1,2-b]furan-10,11-dione
3,3,6-Trimethyl-2,3-dihydro-1H-4-oxa-chrysene-11,12-dione.

9. A process for preparing the compound in accordance with claim 6, wherein the compound, which is represented by Formula 1-1 and in which $R_{11}$ and $R_{12}$ is simultaneously not hydrogen, is synthesized via cyclization of 2-allyl-3-hydroxy-1,4-phenanthrenequinone derivatives in the condition of acid catalyst.

10. The process according to claim 9, wherein the 2-allyl-3-hydroxy-1,4-phenanthrenequinone derivative is synthesized via rearrangement of 3-allyloxy-1,4-phenanthrenequinone derivatives.

11. The process according to claim 9, wherein the 2-allyl-3-hydroxy-1,4-phenanthrenequinone derivative is synthesized via C-alkylation of 3-oxy-1,4-phenanthrenequinone and allyl halide.

12. The process according to claim 10, wherein the 3-allyloxy-1,4-phenanthrenequinone derivative is synthesized via reaction with diene and 2-allyloxy-1,4-benzoquinone.

13. The process according to claim 12, wherein the diene is 1-vinylcyclohexene or styrene derivative.

14. A method of treating at least one disease selected from the group consisting of metabolic syndrome disease, obesity, an obesity complication, a liver disease, arteriosclerosis, cerebral apoplexy, myocardial infarction, a cardiovascular disease, an ischemic disease, diabetes, a diabetes-related complication or an inflammatory disease, comprising administering a therapeutically effective amount of the pharmaceutical compositions in accordance with claim 1 to a subject in need thereof.

15. The method according to claim 14, wherein the diabetes-related complication is selected from the group consisting of hyperlipidemia, hypertension, retinopathy or renal failure.

* * * * *